US009446260B2

(12) United States Patent
Jagger

(10) Patent No.: US 9,446,260 B2
(45) Date of Patent: Sep. 20, 2016

(54) COMPUTER CONTROLLED LASER THERAPY TREATMENT TABLE

(76) Inventor: Mark Jagger, Mississauga (CA)

( * ) Notice: Subject to any disclaimer, the term of this patent is extended or adjusted under 35 U.S.C. 154(b) by 0 days.

(21) Appl. No.: 13/421,433

(22) Filed: Mar. 15, 2012

(65) Prior Publication Data

US 2012/0239059 A1 Sep. 20, 2012

Related U.S. Application Data

(63) Continuation of application No. 13/236,465, filed on Sep. 19, 2011, now abandoned.

(60) Provisional application No. 61/465,200, filed on Mar. 15, 2011.

(51) Int. Cl.
*A61N 5/067* (2006.01)
*A61H 1/00* (2006.01)
*A61N 5/06* (2006.01)
(Continued)

(52) U.S. Cl.
CPC ........... *A61N 5/0613* (2013.01); *A61H 1/0222* (2013.01); *A61B 2018/2085* (2013.01); *A61G 13/009* (2013.01); *A61G 13/08* (2013.01); *A61G 13/121* (2013.01); *A61G 2203/34* (2013.01); *A61G 2203/36* (2013.01); *A61G 2203/40* (2013.01); *A61H 1/0296* (2013.01); *A61H 2201/1607* (2013.01); *A61H 2201/1664* (2013.01); *A61H 2201/1676* (2013.01); *A61N 2005/067* (2013.01); *A61N 2005/0632* (2013.01); *A61N 2005/0644* (2013.01)

(58) Field of Classification Search
USPC .................. 5/600–608; 607/88–94; 606/130
See application file for complete search history.

(56) References Cited

U.S. PATENT DOCUMENTS 776,335 A  11/1904 Langworthy
902,946 A  11/1908 Nise
(Continued)

FOREIGN PATENT DOCUMENTS

KR  WO 02076552 A1 * 10/2002 ......... A61H 23/0245

OTHER PUBLICATIONS

Kaslow, Jeremy. "Lasers—Class IV Therapeutic.". https://web.archive.org/web/20100104151414/http://drkaslow.com/html/lasers_-_class_iv_therapeutic.html. Jan. 4, 2010. Web. Sep. 14, 2015.*

*Primary Examiner* — Lynsey Crandall
*Assistant Examiner* — Nathan A Baldwin
(74) *Attorney, Agent, or Firm* — Thomas A. O'Rourke; Bodner & O'Rourke, LLP

(57) ABSTRACT

A multi-function, adjustable chiropractic table comprises a body section fixed to a table frame. A cervical section is pivotally attached to the table frame and securable at a desired angle. The cervical section comprises a padded head support, forehead strap, and neck bolsters. The head support is slidably mounted in a tray and translatable therein using a scissors mechanism, for linear axial traction. Pivotally mounting the tray to the cervical section permits lateral traction. A four-bar linkage, including a base frame, permits raising/lowering of the table using an actuator activated by a foot triggered wave switch comprising proximity sensors. The body section comprises a chest, lumbar, and leg sections. The chest section is replaceable with a treatment module comprising hot and cold compresses, or a laser enhanced spinal decompression therapy apparatus comprising a laser driven by two linear actuators to emit light according to one or more treatment protocols.

18 Claims, 42 Drawing Sheets

(51) Int. Cl.
*A61H 1/02* (2006.01)
*A61G 13/00* (2006.01)
*A61G 13/08* (2006.01)
*A61G 13/12* (2006.01)
*A61B 18/20* (2006.01)

(56) References Cited

U.S. PATENT DOCUMENTS

| | | |
|---|---|---|
| 1,142,422 A | 6/1915 | Hawley |
| 1,205,649 A | 11/1916 | Miller |
| 1,239,522 A | 9/1917 | Rock |
| 1,374,115 A | 4/1921 | Roemer |
| 2,593,675 A | 4/1952 | Hastings |
| 2,630,800 A | 3/1953 | Voss |
| 2,674,996 A | 4/1954 | Stowell |
| 2,690,175 A | 9/1954 | Daughtry |
| 2,693,796 A | 11/1954 | Warner |
| 2,798,481 A | 7/1957 | Matthews |
| 2,808,049 A | 10/1957 | Graham |
| 2,865,367 A | 12/1958 | Sorenson |
| 3,302,641 A | 2/1967 | Beme |
| 3,570,479 A | 3/1971 | Horn |
| 4,002,165 A | 1/1977 | Lind |
| 4,387,888 A | 6/1983 | Marinakis |
| 4,589,126 A | 5/1986 | Augustsson et al. |
| 4,796,609 A | 1/1989 | Rix |
| 4,951,654 A | 8/1990 | Gambale |
| 4,985,780 A * | 1/1991 | Garnier et al. .......... 219/121.68 |
| 5,014,688 A | 5/1991 | Fast |
| 5,207,216 A | 5/1993 | Sweeney |
| 5,464,436 A | 11/1995 | Smith |
| 5,782,870 A | 7/1998 | McAfee |
| 5,794,286 A | 8/1998 | Scott et al. |
| 6,077,293 A | 6/2000 | King |
| 6,152,950 A * | 11/2000 | Shealy ................. A61H 1/0222 606/241 |
| 6,197,020 B1 | 3/2001 | O'Donnell |
| 6,638,299 B2 * | 10/2003 | Cox ...................... A61H 1/0222 5/617 |
| 6,821,288 B2 | 11/2004 | Schaeffer |
| 6,929,607 B2 * | 8/2005 | Lipman ........................ 600/300 |
| 7,118,563 B2 | 10/2006 | Weckwerth |
| 7,189,214 B1 | 3/2007 | Saunders |
| 7,374,569 B2 | 5/2008 | Whatcott |
| 7,472,441 B1 | 1/2009 | Steffensmeier |
| 7,836,893 B2 | 11/2010 | Holliday |
| 8,033,284 B2 | 10/2011 | Porter et al. |
| 8,273,046 B2 | 9/2012 | Walther |
| 2003/0127440 A1 * | 7/2003 | Egashira ................ 219/121.82 |
| 2004/0010299 A1 | 1/2004 | Tolkoff |
| 2004/0260367 A1 | 12/2004 | De Taboada |
| 2006/0100676 A1 | 5/2006 | Walmsley |
| 2006/0173514 A1 | 8/2006 | Biel |
| 2006/0206046 A1 * | 9/2006 | Saunders .................. A61F 5/04 602/32 |
| 2006/0287627 A1 | 12/2006 | Johnson |
| 2007/0033735 A1 * | 2/2007 | Formenti ......................... 5/600 |
| 2007/0106192 A1 * | 5/2007 | Johnson ............... A61H 1/0222 602/32 |
| 2007/0208289 A1 | 9/2007 | Walther |
| 2007/0208396 A1 | 9/2007 | Whatcott |
| 2008/0039751 A1 * | 2/2008 | Yang ..................... A61H 39/04 601/101 |
| 2009/0254154 A1 * | 10/2009 | De Taboada ......... A61N 5/0613 607/88 |
| 2010/0095455 A1 * | 4/2010 | Brinkerhoff et al. ............. 5/600 |
| 2010/0324426 A1 * | 12/2010 | Tucek .................. A61B 5/0064 600/476 |
| 2011/0057122 A1 * | 3/2011 | Moyers ..................... 250/491.1 |

* cited by examiner

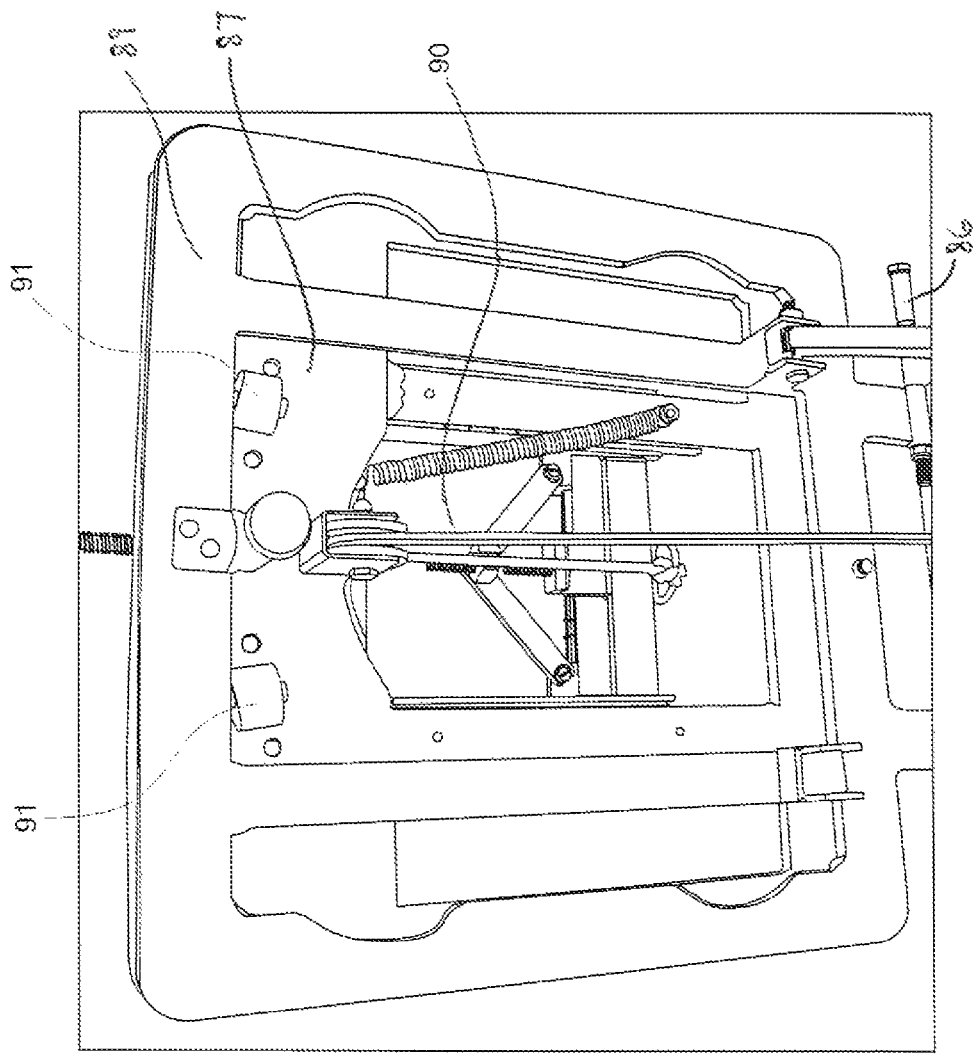

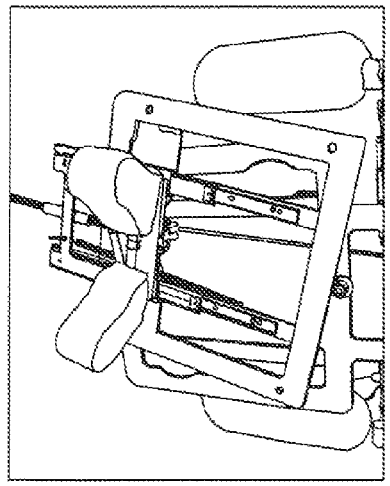
FIG.5I
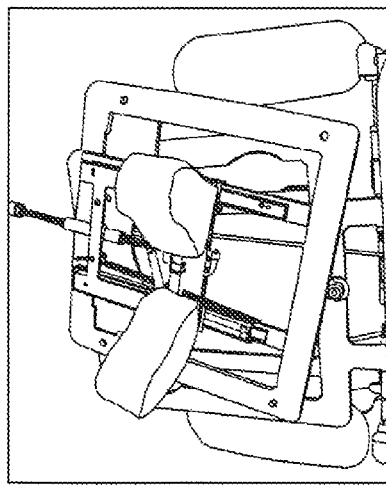
FIG.5H
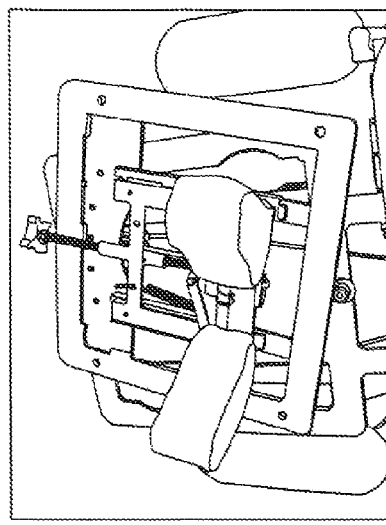
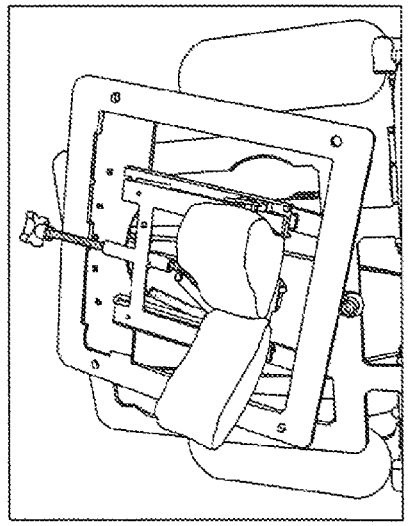
FIG.5L
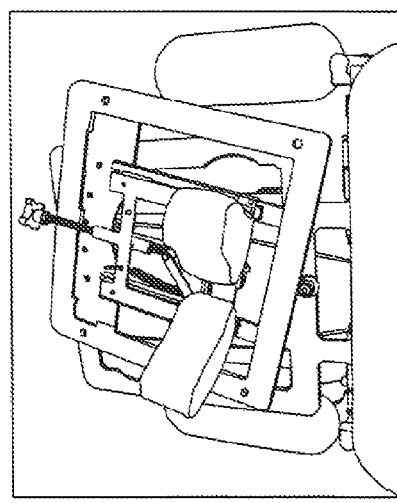
FIG.5K
FIG.5J

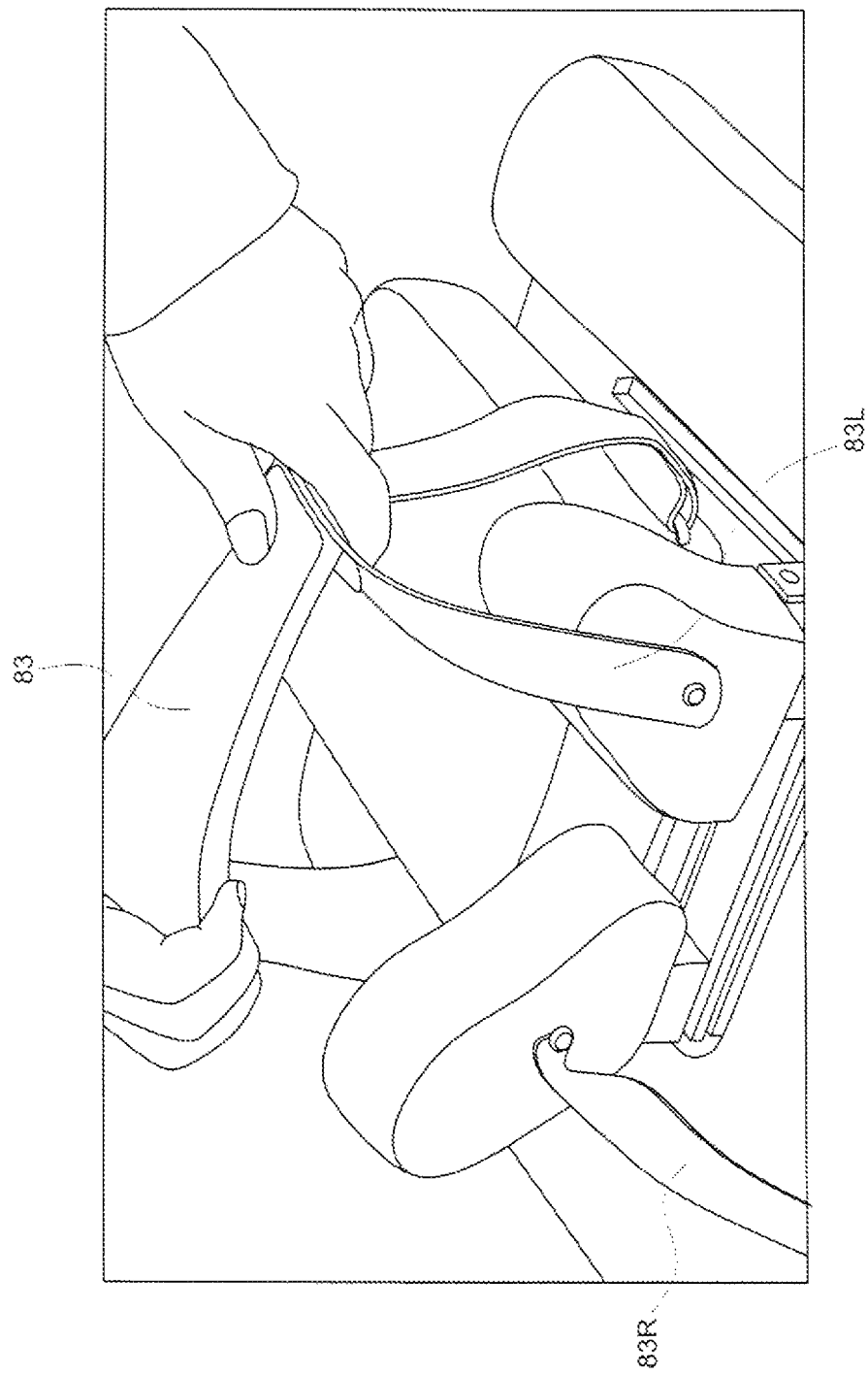

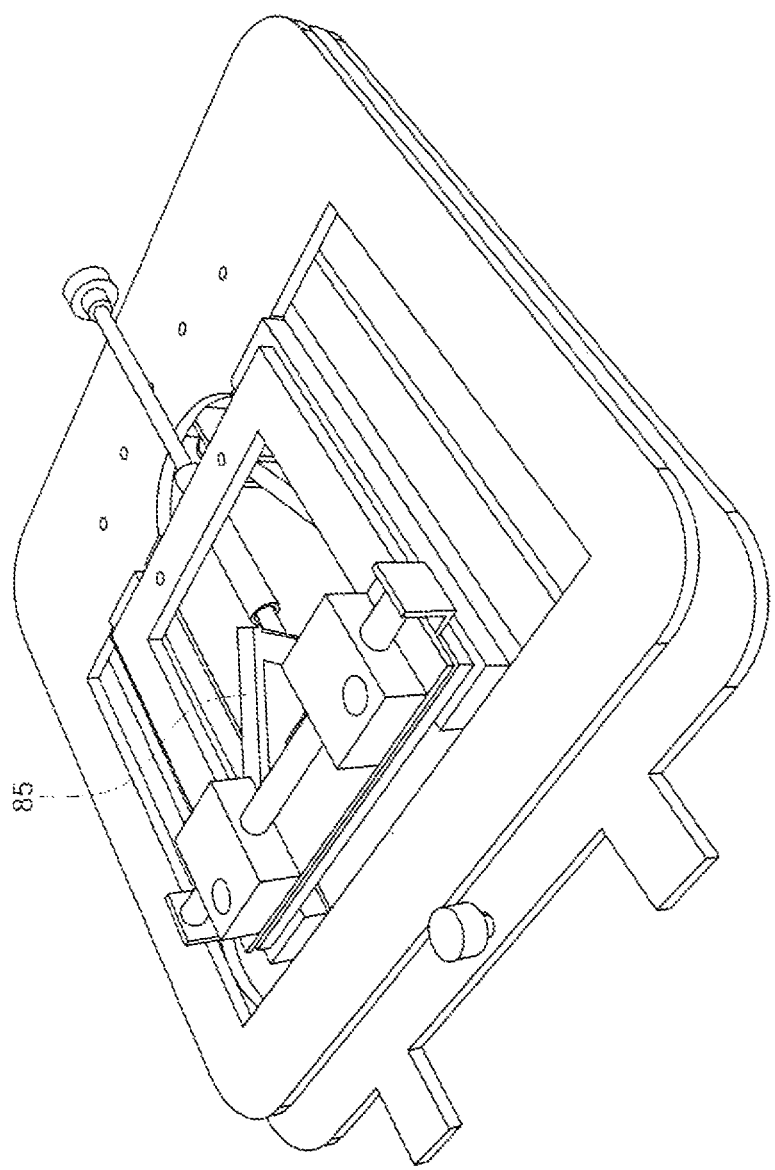

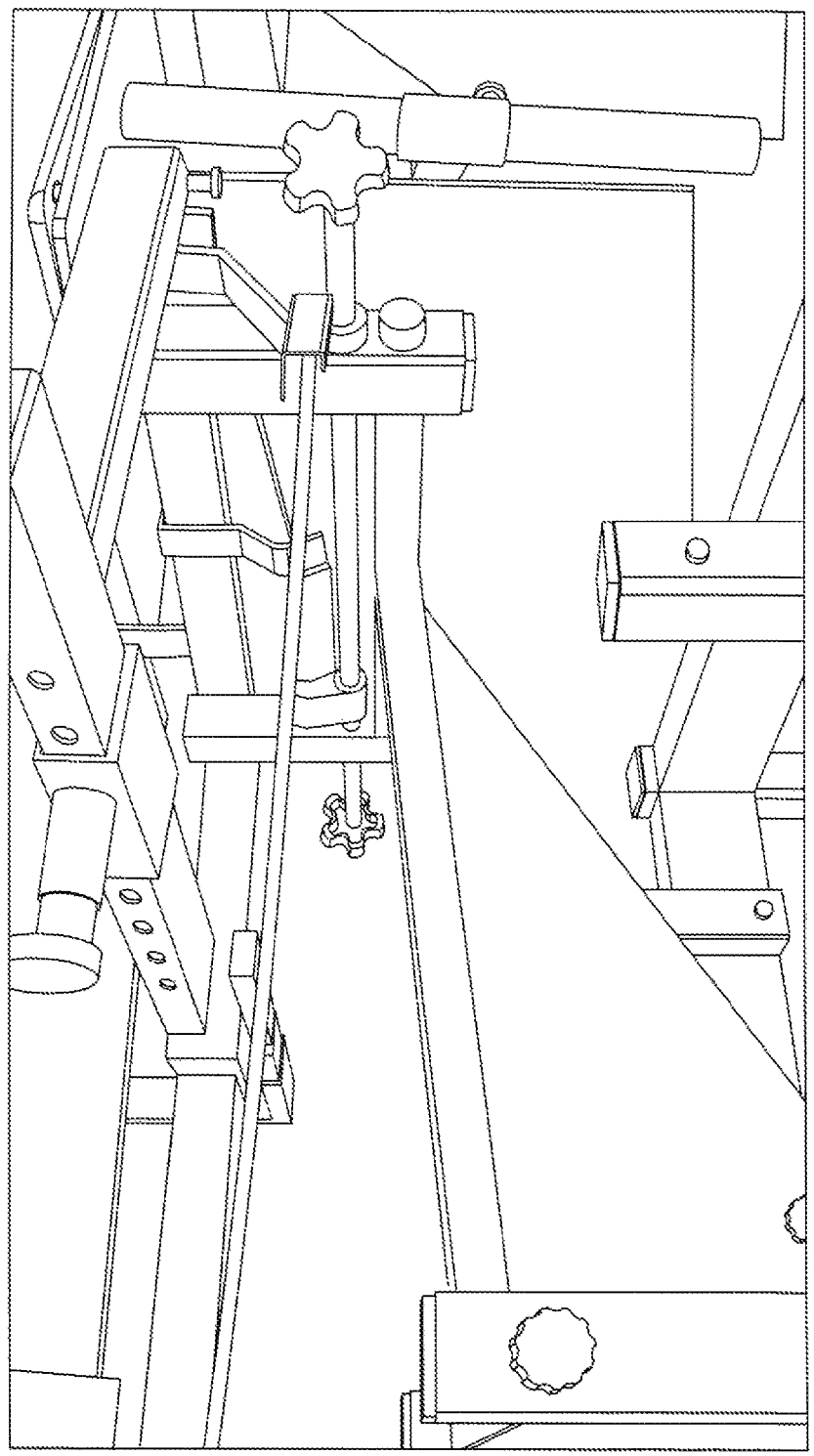

Left Sided Lumbar Disk Bulge or Herniation

Spinal Decompression For Central Disc Injury Or Central LBP

Spinal Decompression For Lateral Disc Injury, LBP and Radiculopathy

Right Sided Lumbar Disk Bulge or Herniation

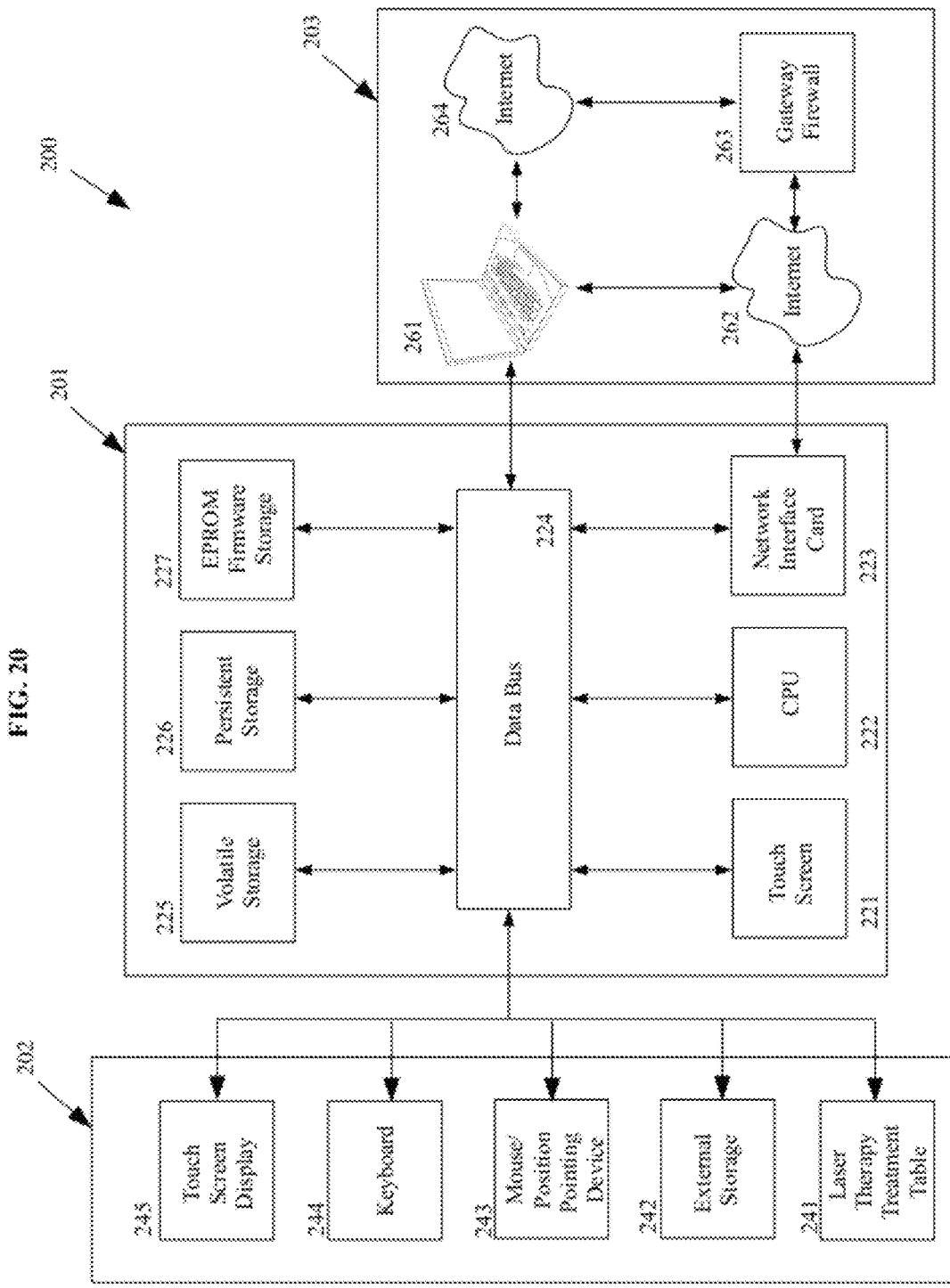

COMPUTER CONTROLLED LASER THERAPY TREATMENT TABLE

CROSS REFERENCES TO RELATED APPLICATIONS

This application claims priority on U.S. Provisional Application Ser. No. 61/465,200, filed on Mar. 15, 2011, titled "Innovations to Multi-Functional Medical/Rehabilitation Treatment Tables, Protocols and Associated Equipment," and is a continuation of U.S. Application Ser. No. 13/236,465, titled "Improved Multi-Function Medical/Rehabilitation Treatment Table and Equipment," filed on Sep. 19, 2011 now abandoned, with the disclosures of each incorporated herein by reference.

FIELD OF THE INVENTION

The present invention relates to the field of therapy tables, and more particularly to apparatus which are capable of providing increased performance capability for a medical practitioner while reducing the therapist's workload.

BACKGROUND OF THE INVENTION

Treatment tables are commonly used in various different medical fields, including the manual-therapy professions, such massage therapy, osteopathy, and physical therapy, and also for chiropractic medicine. Particularly for chiropractic treatments, a table may be necessary for a practitioner to perform certain examinations, adjustment, and procedures, as chiropractic physicians generally focus on the management of the neuro-musculoskeletal system without using medicines or surgery. Although the emphasis of such manual therapy may often be on the spine, for effective treatment of low back pain, lumbar disc herniation, etc., treatment may also be received on the cervical region for neck pain, some forms of headache, etc.

Therefore, treatment tables have been utilized for some time in these practices, with a typical example of such a chiropractic tables generally being illustrated within FIG. 1 of U.S. Pat. No. 7,472,441 to Steffenmeier for "Automatic Tilt-Elevating Chiropractic Table." However, despite the patentable and other advances that have been made to date, they have not developed sufficiently to support newer treatment techniques or to be able to provide the versatility and comfort level that is expected and needed by chiropractic patients. These deficiencies are addressed by the invention disclosed herein.

OBJECTS OF THE INVENTION

It is an object of the invention to provide a manual therapy treatment table, where the table is capable of being raised and lowered to suit the practitioner.

It is a further object of the invention to provide an improved means of triggering an actuator to extend or retract to raise or lower the table, which may occur by a conventional hand switch, a conventional foot pedal switch, and/or a wave switch system of the present invention which simply requires the practitioner waving a foot close to a tube.

It is another object of the invention to provide a manual therapy treatment table that includes an adjustable cervical section capable of linear axial traction, and also being capable of performing lateral traction as well.

It is a further object of the invention to provide a caster system being slidably attached to a base frame to be moveable between a first position where the casters are deployed and permit sliding transport of the table, and a second position where the casters are retracted and the frame provides stable static support for the table.

It is another object of the invention to provide a cervical section head support offering improved padding and greater comfort provided by adjustable neck bolsters, as well as a three-point head strap to permit better securing of a patient's head without excessive tightening inherent in a conventional single strap system.

It is also an object of the invention to provide a pivotal traction platform to facilitate lateral traction for decompression therapy at a desired angle.

It is another object of the invention to provide a chest section, a lumbar section, and a leg section, each of which may be split into a fixed lower portion, and a removable upper padded portion that may be where replaceable with a treatment module.

It is also an object of the invention to provide an improved means of applying hot and cold compresses, through the use of electrically powered heating and cooling in a specialized treatment module.

It is another object of the invention to provide a treatment module permitting laser enhanced spinal decompression therapy.

Further objects and advantages of the invention will become apparent from the following description and claims, and from the accompanying drawing figures.

SUMMARY OF THE INVENTION

A multi-function, adjustable chiropractic table may comprise a table frame, a body section being fixedly secured to the table frame to support a patient's body, and a cervical section. The cervical section may be pivotally attached to a first end of the table frame to permit rotation relative to the body section, and may be secured to be at a desired angle with the table frame. A left arm pad with a bolster protruding upward therefrom, and a right arm pad with a bolster protruding upward therefrom may each be adjustably mounted to the table frame to be independently adjustable both medially and laterally, and they may also be independently adjustable both cephalically and caudally.

A padded head support may be mounted in an opening in a tray, with the tray being mounted to a plate of the cervical section. A forehead strap may be secured to the padded head support, and a pair of neck bolsters may also be pivotally mounted to the padded head support. The head support may be slidably mounted in tracks of the tray so as to be translatable relative to the tray, to thereby accomplish linear axial traction. The tray may be pivotally mounted to the cervical section to thereby accomplish lateral traction.

The multi-function adjustable chiropractic table may comprise a mechanism to permit the body section to be elevated and lowered, to accommodate the practitioner and patient. The mechanism may be constructed as follows. A first pair of mechanism supports and a second pair of mechanism supports may be fixed to a base frame, and may protrude upward therefrom. A first arm may have a first end being mounted to the first pair of mechanism supports to thereby be pivotable about a first axis, and the second end of the arm may be pivotally connected to the table frame. Also, a second arm may have a first end mounted to the second pair of mechanism supports to thereby be pivotable about a second axis, and the second end of the second arm may also be pivotally connected to the table frame. An actuator may have a first end be pivotally mounted to a portion of the base frame, and a second end be pivotally mounted to a portion of the first arm at a point being eccentric to the first axis. A connecting link may be pivotally connected to the first arm at a point being eccentric to the first axis, and may also be pivotally connected to the second arm at a point being eccentric to the second axis so that the motion of the second arm is slaved with movement of the first arm. So extension of the actuator drives the first arm and the slaved second arm to causes raising of the table frame, and retraction of the actuator causes lowering of the table frame.

Triggering the actuator to extend or retract to thereby raise or lower the table may occur by one or more of a conventional hand switch, a conventional foot pedal switch, and a wave switch system of the present invention. The wave switch system may comprise either one or more sensor tubes positioned peripherally about the base frame, such that the raising/lowering of the table occurs by waving of a foot to toggle the sensor tube in either of two different directions.

The multi-function adjustable chiropractic table may further comprise two or more casters being slidably attached to the base frame and being moveable between a first position and a second position, where in the first position, each of the casters extends below the base frame with the casters supporting the table, and where in the second position, each of the casters are positioned above a bottom surface of the base frame and the base frame supports the table. Each of the two or more casters may have a linear actuator to cause the movement between the first and second positions, where the linear actuators may be simultaneously activated by a switch.

The multi-function adjustable chiropractic table may further comprise a traction platform being pivotally secured to the base frame in proximity to the table frame at the end which opposite to the end having the cervical section attached thereto. The traction platform may be laterally adjustable using either a tension knob on the platform being securable to a plate on the base frame, or using a locking pin on the platform being received in one of a plurality of holes in the plate. The traction platform may facilitate a machine for providing lateral traction for decompression therapy at a desired angle.

The body section of the chiropractic table, described above, may further comprise a chest section, a lumbar section, and a leg section. Each of the chest section, the lumbar section, and the leg section may comprise padding. Any of these sections, and particularly the lumbar section, may be split into a fixed lower portion and a removable upper padded portion, where the removable upper padded portion may be replaceable with a treatment module being secured to the fixed lower section. The treatment module may be traditional hot and cold compresses, or may comprise electrically powered heating and cooling.

A novel treatment module may comprise a laser enhanced spinal decompression (LESD) apparatus being secured to the base portion of the lumbar or other sections, including the cervical section. The apparatus for the laser enhanced spinal decompression apparatus may comprise a first linear actuator and a second linear actuator, which may be usable to position the laser along an X direction (medially and laterally) and along a Y direction (cephalically and caudally) for unassisted treatments. The laser as well as the first and second linear actuators may preferably be mounted within an enclosure or box. The laser box may have a cushioned gland around a top perimeter of the box to serve in creating a seal against a patients' skin surface to thereby reduce or eliminate the escape of any laser light.

The laser may emit laser light upon a spine of a patient, with the laser translating in the X and Y directions and being directed to emit light according to patient-specific or protocol-specific treatment requirements. The laser enhanced spinal decompression apparatus may further comprise a controller that interfaces with a computer operating system to permit the treatment protocols to be pre-programmed and/or customized. A range of motion for the laser light of one treatment protocol may comprise travel of approximately 8 inches or more to each side of a center of a patient's spine, and travel up and down a patient's spine to cover spinal disks from L1 to S1 (Note—The table may be configured to facilitate laser treatment of each of the thirty-three human vertebrae). The laser enhanced spinal decompression apparatus may also include one or more sensors, such as proximity sensors, optical sensors, temperature sensors, pressure sensors, and motion sensors, which may be usable for ensuring proper treatment. For example, one or more temperature sensors may be used for thermographic imaging to monitor tissue temperatures to achieve an optimal dosage.

BRIEF DESCRIPTION OF THE DRAWINGS

FIG. 5G is a bottom view of the cervical section.

FIG. 5H is top view of the cervical section of FIG. 5G, with the padding removed to expose the scissors mechanism for the neck bolsters, and with the head support and neck bolsters shown in a position proximal to the chest section, and with the neck bolsters shown substantially separated.

FIG. 5I is the top view of FIG. 5H, but with the head support and neck bolsters moved by the cable/rope and pulley system to be in a position less proximal to the chest section.

FIG. 5J is the top view of FIG. 5I, but with the head support and neck bolsters moved by the cable/rope and pulley system to be in a position distal to the chest section.

FIG. 5K is the top view of FIG. 5H, but with the neck bolsters moved by the scissors mechanism to be closer together.

FIG. 5L is the top view of FIG. 5K, but with the neck bolsters moved by the scissors mechanism to be touching each other.

FIG. 7 is a perspective view of the cervical section showing the rotatable neck support bolsters attached and in proper relation to the padded head support, along with a head strap extending from the head support, and secondary straps extending from the neck bolsters and having Velcro thereon to thereby be securable to the head strap.

FIG. 8A is a top perspective view of the scissors-style mechanism of the cervical section tray, usable to provide adjustments to the neck bolsters.

FIG. 11 is a perspective view looking up at the underside of the table, to show adjustable attachment details of the bolstering and arm rest system.

FIG. 20 is a schematic of an exemplary computing unit being capable of running the software of the current invention and interacting with other computers over the internet, and with external peripherals, including specialized equipment of the treatment table of the current invention.

DETAILED DESCRIPTION OF THE INVENTION

Figure 1A:
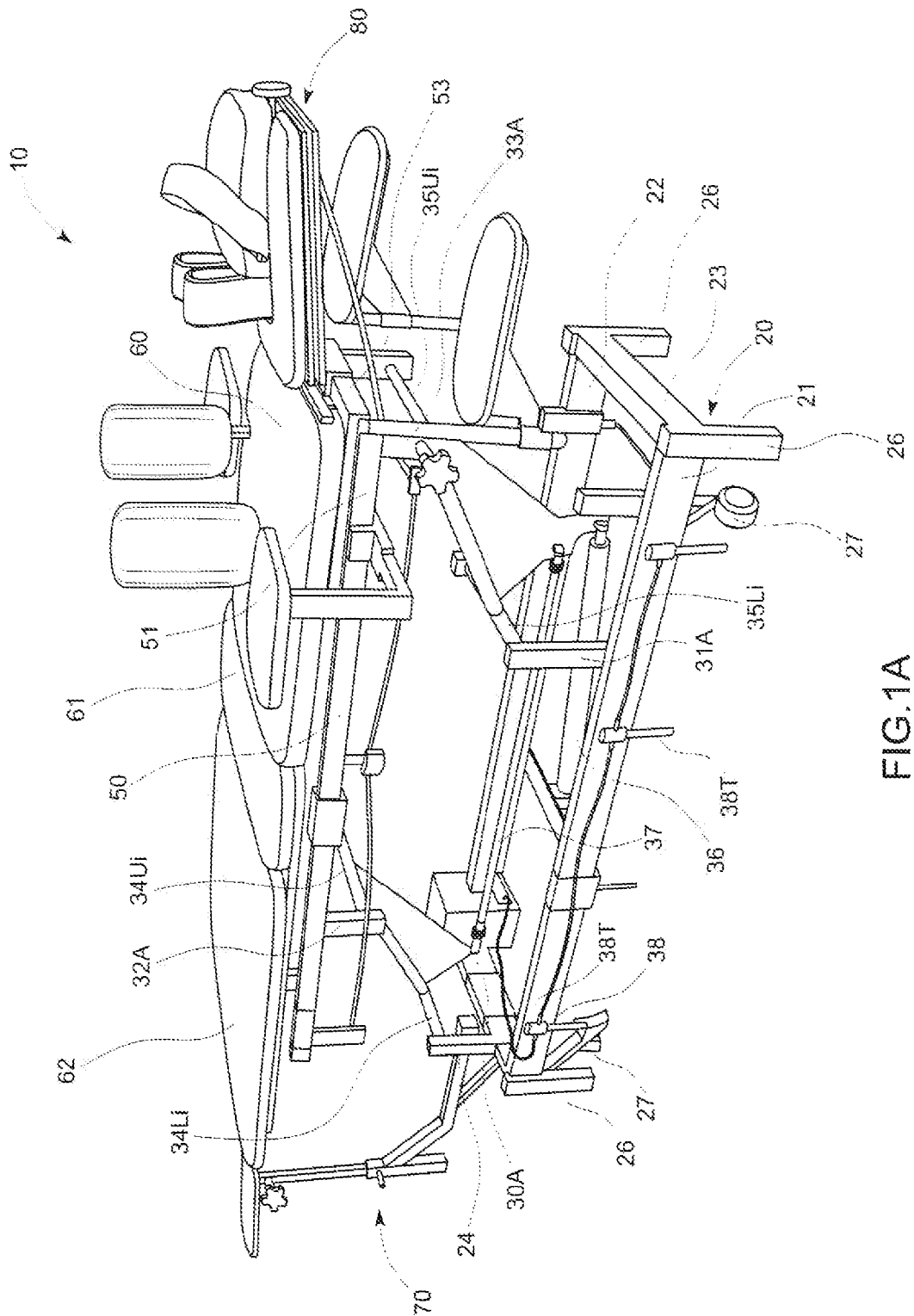
FIG. 1A is a perspective view of the multi-functional treatment table of the present invention.

FIG. 1 shows a first embodiment of the multi-function adjustable treatment table assembly 10 of the present invention. The table may comprise a base (support) frame 20 which may be made of a single unitary piece, perhaps being a machined part or a cast part, and potentially forming a race-track shape. In general, the base frame 20 may form at least a first elongated side 21 and a second elongated side 22, which may be connected by a first cross-member 23 and a second cross-member 24. Where four separate elongated sides 21 and 22, and separate cross-members 23 and 24 are utilized, they may be secured together using any suitable mechanical fasteners, or they may be welded together.

Extending downward from the base frame 20 may be four support legs 26 being fixed to the frame, and preferably spaced about the frame to provide stable support. In one embodiment, the legs 26 may be at a location proximal to the joining of the sides 21 and 22, and cross-members 23 and 24. The multi-function adjustable chiropractic table 10 may further comprise two or more casters 27 being slidably attached to the base frame 20 so as to be moveable between a first position and a second position. The first position may be a lowered position where each of the casters 27 extends below the bottom surface of the base frame 20 to contact the ground and thereby support the table. The second position may be a raised position where the bottom of each of the casters 27 is positioned above the bottom surface of the base frame, so that the base frame is resting upon the ground. Each of the casters 27 may have a linear actuator to drive the movement between the first and second positions, and to lock the casters at each of those positions. The linear actuators may be simultaneously activated by a foot/hand switch. In a preferred embodiment, there may be four casters, with one being located proximate to each of the four legs 26, which, when deployed down to be in the first position, may permit rolling movement and relocation of the table assembly 10.

A body support section of table assembly 10 may be fixed to a table frame 50, and may comprise a chest section 60, a lumbar section 61, and a leg section 62 with each of those sections comprising a rigid support plate and padding thereon. The table frame 50 may be formed similar to the base frame 20, to be a single member, or it may be a build-up of four different members-two side members 51, 52, and two cross-members, 53, and 54. Raising and lowering of the body support section—the table frame 50 mounted chest section 60, lumbar section 61, and leg section 62—may be relative to the statically positioned base frame 20, and may occur through the use of a mechanism connecting the base frame 20 and the table frame 50. In a simple embodiment, a pair of arms may each have a first end be pivotally connected to the base frame 20 and have a second end be pivotally connected to the table frame 50.

In a preferred embodiment, table assembly 10 may have a first lower pair of mechanism supports, being first support 30A and second support 30B, and a second lower pair of mechanism supports, being third mechanism support 31A and fourth mechanism 31B, with each of those supports being fixed to the base frame 20, using fasteners or by welding, to protrude upward therefrom. Similarly, table assembly 10 may have a first upper pair of mechanism supports 32A and 32B, and a second upper pair of mechanism supports 33A and 33B, with each of those supports being fixed to the table frame 50, using fasteners or by welding, to protrude downward therefrom. A first arm 34 may have a first end and a second end. The first end may comprise pins 34Li and 34Lii protruding from opposite sides of the arm 34 to be concentric with a first axis, for pivotal mounting within the first lower pair of mechanism supports 30A and 30B. The second end may comprise pins 34Ui and 34Uii protruding from opposite sides of the arm 34 for pivotal mounting within the first upper pair of mechanism supports 32A and 32B. A second arm 35 may have a first end and a second end. The first end may comprise coaxial pins 35Li and 35Lii protruding from opposite sides of the arm 35 to be concentric with a second axis, for pivotal mounting within the second lower pair of mechanism supports 31A and 31B. The second end may comprise pins 35Ui and 35Uii protruding from opposite sides of the arm 35 for pivotal mounting within the second upper pair of mechanism supports 33A and 33B.

Figure 1C:
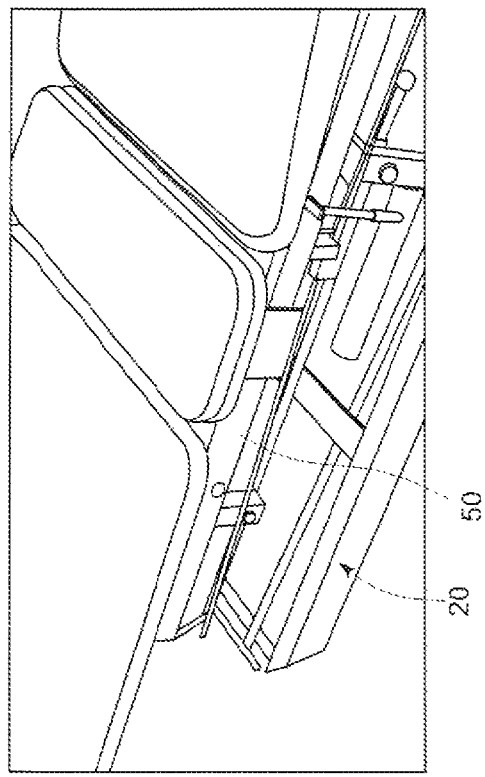
FIG. 1C is a perspective view showing the table of the present invention in a position prior to being lowered.
Figure 1D:
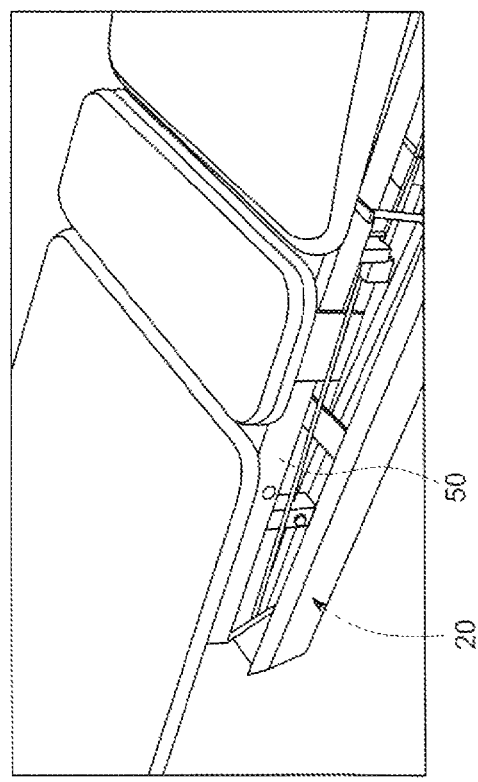
FIG. 1D is a perspective view showing the table of FIG. 1C after being actuated to be in a lower position.

An actuator 36 may have one end pivotally connected to the base frame 20, and a second end pivotally connected to the second arm 35 at a point being eccentric to the second axis. A connecting link 37 may have a first end be pivotally connected to the first arm 34 at a point being eccentric to the first axis, and may also have a second end be pivotally connected to the second arm 35 at a point being eccentric to the second axis to thereby slave the motion of the second arm to that of the first arm, when the first arm is actuated by actuator 37. With this arrangement, extension of the actuator 37 may result in elevating of the upper frame 50 and body support sections, and retraction of the actuator may conversely cause lowering of the upper frame (FIGS. 1C-1D). As the table 10 will generally be stationary, movement of the body support section may thus occur through rotation of the first arm about the first axis centered on pins 34Li and 34Lii, and by rotation of the second arm about the second axis centered on pins 35Li and 35Lii.

A modular power supply system may be utilized for the actuator/motor drive 37, to raise and lower the table, which exhibits proven reliability, safety, and ruggedness. A separate power supply, and control system allows inclusion of safety and control features, which enhance user friendliness and operational efficiency. A DC power supply/control system 12/24 volt mode gives increased lift capacity, while a 12 volt mode for lowering, gives reliable braking function for safe lowering.

Figure 1B:
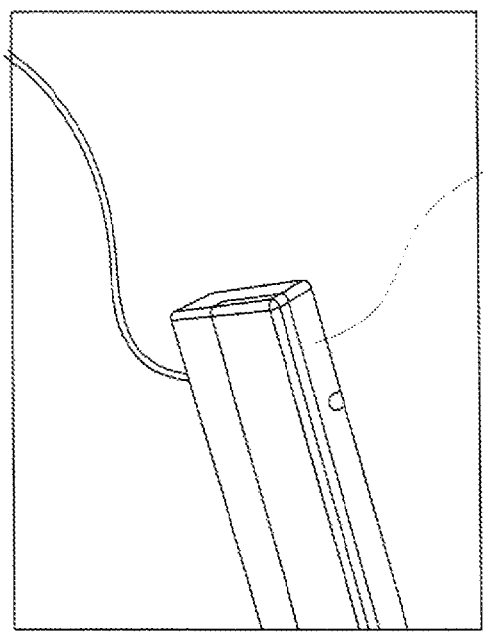
FIG. 1B is a perspective view showing a foot pedal usable for raising and lowering of the table.

A foot pedal 37, as seen in FIG. 1B, may comprise a switch that controls actuator extension and retraction, to cause elevating and lowering of the table. The foot pedal may be replaced by or complemented through the use of what is termed herein as a "wave switch system," where a slight wave of the operator's toe is all that is needed to trigger the actuator 36 to raise or lower the table. The wave switch 38 may be mounted on the base frame 20 at one to four, or even different places, and may be connected with a daisy-chain expandable/retractable electronic harness. A mounting bracket for each of the switches may be moveable to a particular desired position on the base frame 20. For any desired height adjustment of the table, all that is needed is a wave of the toe, against a resilient (rubberlike) tube 38T.

The tube 38T may be made from flexible, semi-rigid material that attaches to a pendulum-like mechanism within the body of the switch at one end that attaches to the base frame 20, while the other end of the tube extends down to approx ½" to 1" above the floor when the table is resting on the base frame 20 (not being supported by the casters 27). The wave switch 38 is intended to replace traditional hand switches (thus freeing up practitioners' hands) and traditional foot switches, that often get left in awkward, inconvenient places, making it difficult for the practitioner to spontaneously change the height of the table, particularly since the practitioner may also wish to freely move around to different areas of the table and nonetheless retain the ability to adjust the table's height while applying treatments. The wave switches 38 can be "daisy chained" with flexible cabling around the bottom rail of the base frame so that a switch is located at regular intervals around the table.

The practitioner simply pushes the tube 38T with the side of his foot in one direction to activate the system to raise the table, and conversely pushes the tube 38T in the opposite direction to lower the table. The tube 38T is designed to be flexible to allow an object, such as a practitioner's foot, to push it in any direction, and even push it past the intended range of motion, without breaking or stressing the components of the switch. The pendulum that the tube is attached to may be spring-biased to return the tube to its center position, which is typically the "off" position. The switching components inside the housing of the "wave switch" may be a mechanical device (push button or lever), or may be a magnetic device, or may even be a proximity sensing device, all of which may be activated when the tube/pendulum is pushed in either direction to make contact with the internal switching target area. The switches may be connected together and connected to the power controller 40 (FIG. 1) with modular disconnect cabling that receives the signal from the switch to activate and power the actuator 36 that raises or lowers the table.

Figure 18:
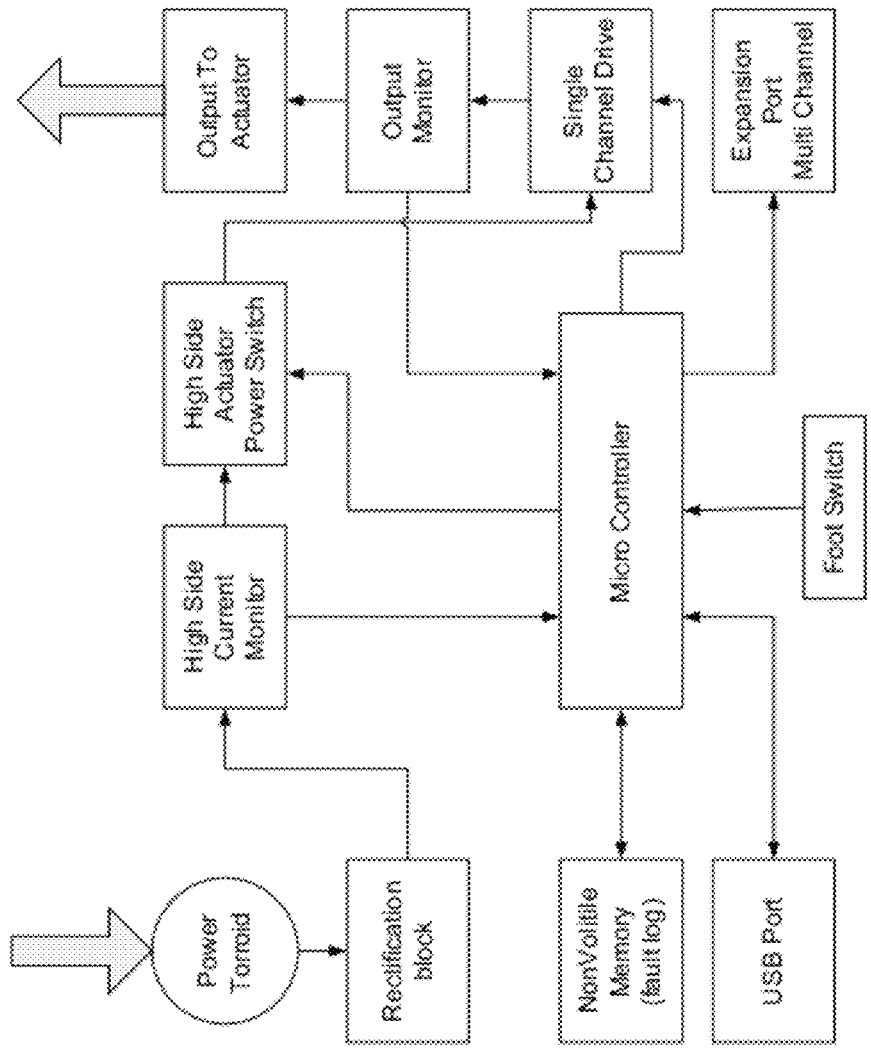
FIG. 18 is a block diagram of the control system of the multi-functional treatment table of the present invention.

The power (micro) controller 40 herein will comprise solid state electronics and add advanced features such as a over temperature and over current shut down, and fault diagnostics with safe shut down will be included. A set of LEDs may be used for user indication of system status. A system log may be maintained in the controller. This log can be retrieved via a common USB memory stick. This data can be sent back to the table's manufacturer via a simple email attachment. The log will contain system build information, fault information, and a usage log. The power controller 40 may comprise other new capabilities (FIG. 18), including a web interface for large institutions and practitioners to see usage reports from each table—reports that quantifies the usage of each table for maximum efficiency. This may also include:

Remote access to adjust table functions and trouble-shoot through an internet portal;
Options to create a link to the internet may include the following:
    Ethernet connection, wireless connections such network card, blue tooth, cellular connection, USB internet access stick, etc.;
Greater automation of table functions, such as pad adjustments;
A user interface device that plugs into the power controller, with a display and buttons/switches or touch screen for controlling, monitoring and adjusting functions and seeing relevant information, such as patient information, pre-set functions, treatment protocols, etc; and
Data storage and retrieval of patient information as it relates to treatment protocols and practitioner requirements.

Extending from one end of the upper frame 50, and being adjacent to chest section 60, may be a cervical section 80, which is shown in greater detail in FIGS. 5A-5F. The cervical section 80 may be pivotally attached to a first end of the upper frame 50 to permit rotation and securing of the cervical section (angled upward or downward) at a desired angle with respect to the body support section, and may be locked into position with a locking gas spring or locking pin and or lever 86 (FIG. 5G).

The cervical section 80 may comprise a padded head support 81. Adjustable neck bolsters 82L and 82R mount at each side of head support 81. The custom bolsters 82L and 82R are designed to be positioned at each side of the patients' neck at the base of the skull and are padded, contoured and adjustable for a comfortable fit for each patient. The cervical section 80 further comprises a unique fully adjustable three-point cervical retainer strap system (FIG. 7) to hold the patient's head snugly, yet comfortably. This addresses a problem with current traction device strapping systems, which are inadequate for securing patients with different head sizes and shapes, particularly for a patient with a sloping forehead, which generally results in the strap sliding across the forehead during traction. This three-point cervical retainer strap system may include one wide over-forehead strap 83 to secure the patients head and two smaller temporal straps, 83L and 83R, which are respectively secured to the bolsters 82L and 82R and may fasten to the over-forehead strap to prevent it from translating. Securing to the strap 83 may be using snap fasteners, Velcro, or any other suitable fastening system. Also, strap 83 may be a single elastic strap, or may alternatively be a split strap with Velcro attached respectively to each end to be securable about a patient's forehead. As a result of this arrangement herein, practitioners no longer need to secure a single strap around a patient's forehead so tightly, as had been necessary with other tables, and which tended to cause patient discomfort. Thus this strap/bolster/padded support arrangement generally improves upon the treatment imparted to the patient.

Figure 8B:
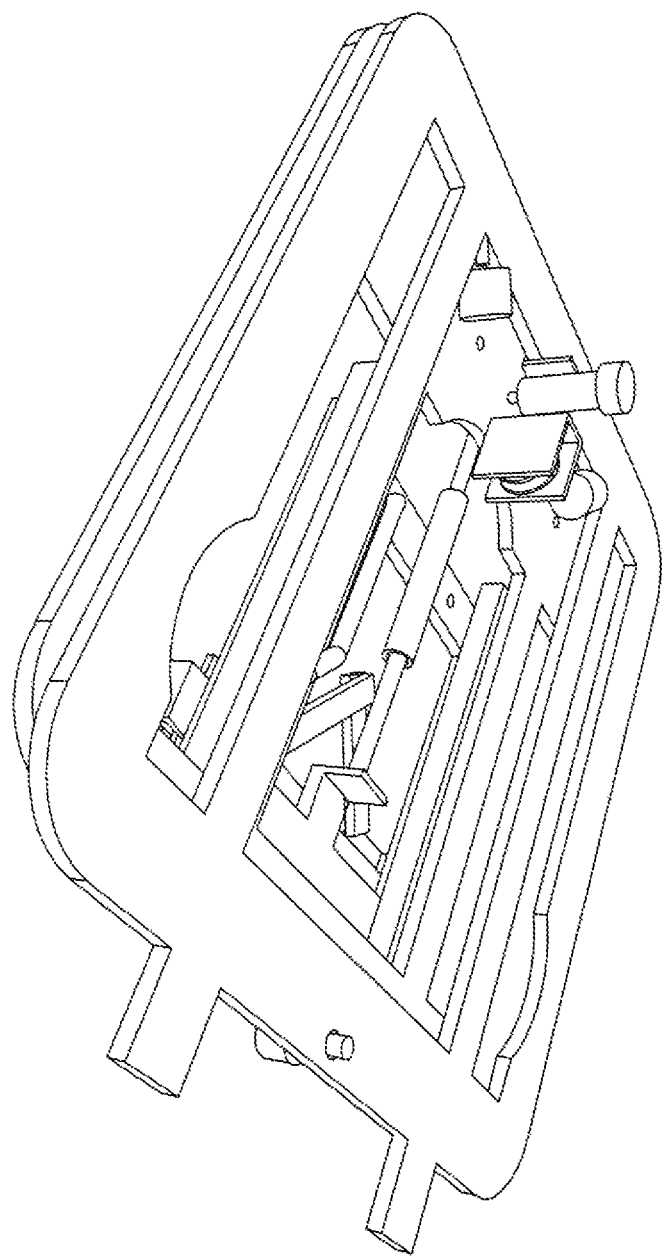
FIG. 8B is a bottom perspective view of the scissors-style mechanism of FIG. 8A.

Adjustment of the neck bolsters 82L/82R inward or outward to accommodate different sized patients may occur through the use of a scissors mechanism 85, which is shown in FIG. 8 during its sub-assembly, and which operates similarly to the arrangement in expired U.S. Pat. No. 4,089,435 to Corompt for "Transportation Equipment," the disclosures of which are incorporated herein by reference. The winding knob and threaded rod combination 84 of FIG. 5D may be rotated to adjust the bolsters inward or outward.

Figure 5A:
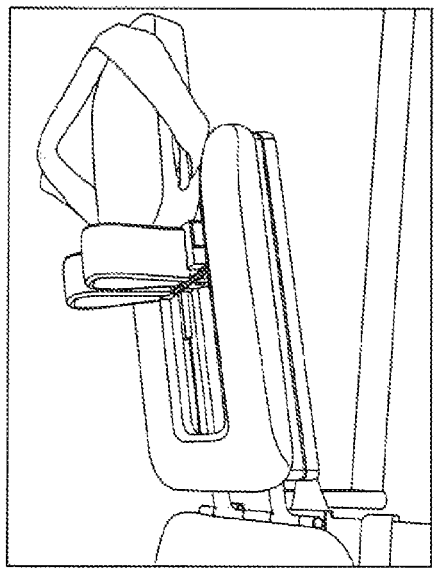
FIG. 5A is a perspective view of a padded head support of an adjustable cervical piece, being in a first position that is proximal to the chest section.
Figure 5B:
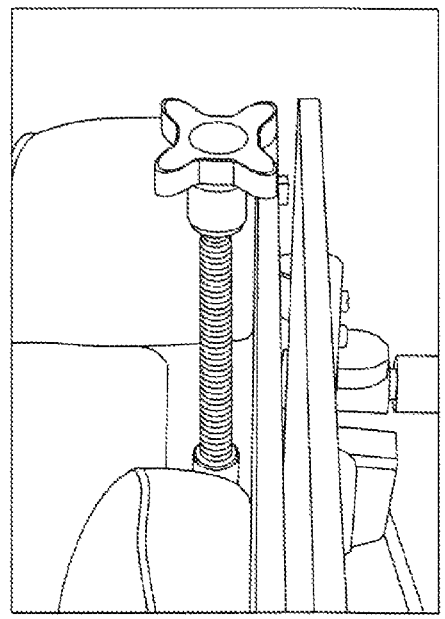
FIG. 5B is the perspective view of the padded head support of FIG. 5A, adjusted to provide traction and being in a second position, being at an extreme limit of travel for the support.
Figure 5C:
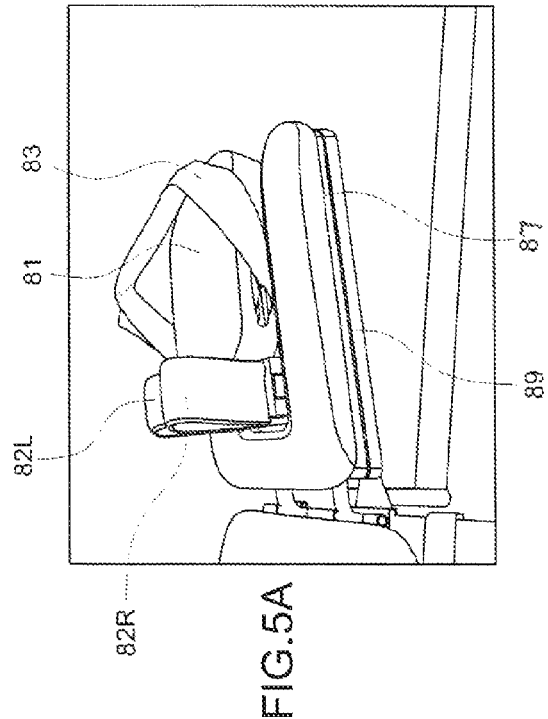
FIG. 5C is the perspective view of the padded head support of FIG. 5A, adjusted to provide traction, and being between the first and second positions.
Figure 5D:
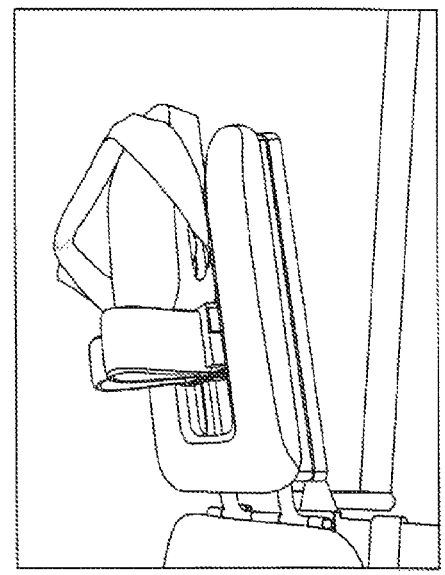
FIG. 5D is a perspective view showing a winding knob being usable to drive a scissors mechanism to actuate the neck bolsters of the head support.
Figure 5F:
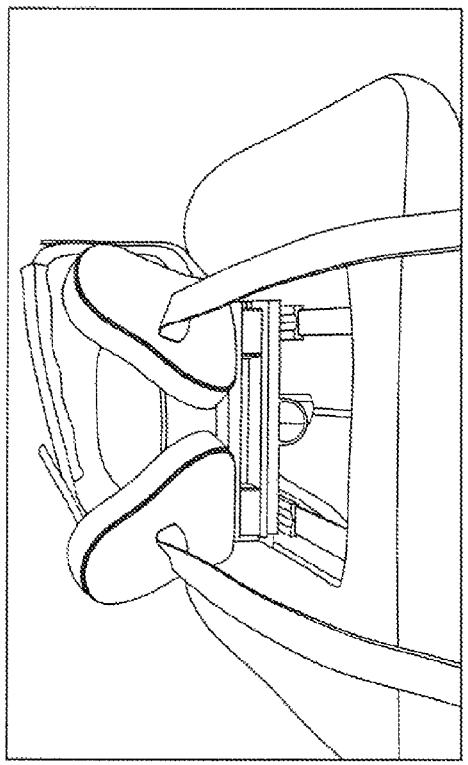
FIG. 5F is a side view of the cervical section with padded head support of FIG. 5B.
Figure 5E:
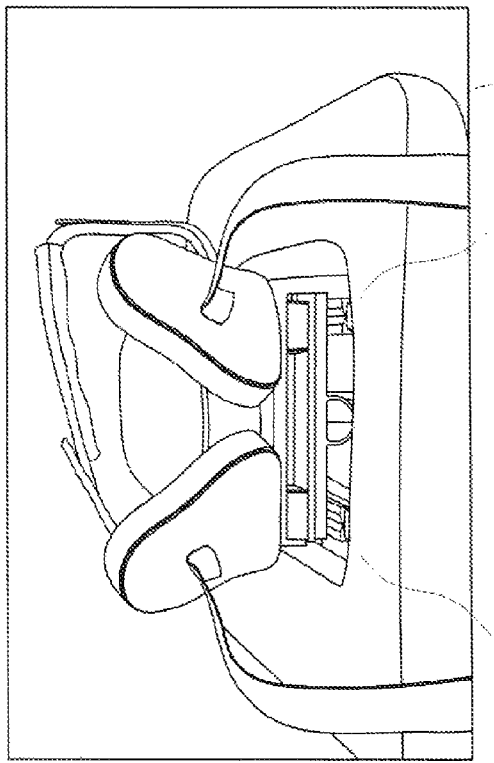
FIG. 5E is a side view of the cervical section with padded head support of FIG. 5C.

As seen in FIGS. 5E and 5F, the head support 81 may be mounted in tracks 88L and 88R of a tray 87 that is mounted to a plate 89 of the cervical section, which is pivotally mounted to the table frame 50 using hinges. This sliding arrangement may be used to facilitate linear axial traction. The padded head support 81 may be translatable in the tracks 88L and 88R relative to tray 87, by using a traction cable or rope 90 that runs along a pulley system attached to the mechanisms of the head support 81, and which runs along the length of the table 10 to the foot of the table. This innovation ensures proper and comfortable patient positioning, and ensures a minimal need for the patient to change positions to participate in other therapies that are disclosed herein.

Figure 6A:
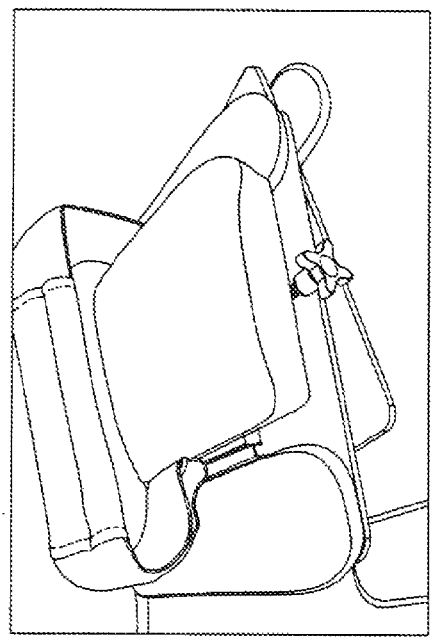
FIG. 6A is a reverse side view of the cervical section of FIG. 5A, with the cervical section being in a neutral position and not providing any lateral traction.
Figure 6B:
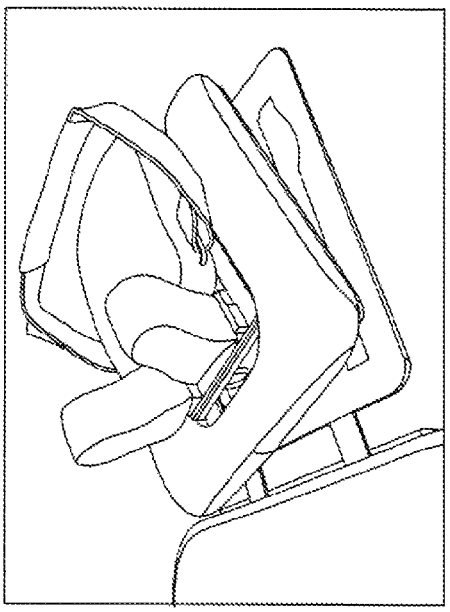
FIG. 6B is the side view of the cervical section of FIG. 6A, but with the tray of the cervical section having been rotated to provide lateral traction, and apply tension to the patient's right side.
Figure 6C:
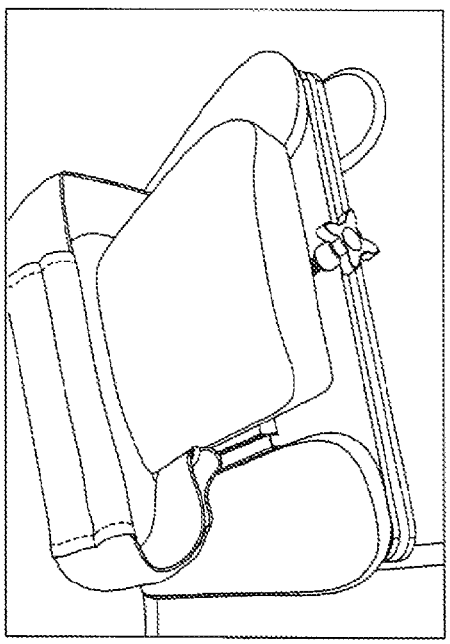
FIG. 6C is the side view of the cervical section of FIG. 6A, but with the tray of the cervical section having been rotated to provide lateral traction, and apply tension to the patient's left side.
Figure 6D:
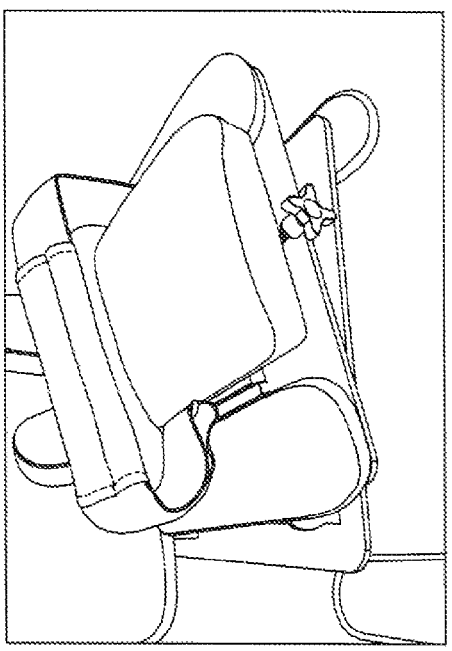
FIG. 6D is a perspective view of the arrangement of FIG. 6C.

Another unique innovation relating to the cervical section 80 is derived from the tray 87 being pivotally mounted to the plate 89 to permit lateral rotation of the padded head support 81 of at least 15 to 30 degrees from each side of center to facilitate lateral cervical spinal decompression (FIGS. 6A-6C). The tray 87 and padded head support 81 may swivel from side-to-side on roller wheels 91 (FIG. 5G) located on the plate 89, which acts as a platform. A spring loaded knob/pin 92 under the plate 89 (FIG. 5D) may lock the tray 87 relative to the plate, once it into the desired position. This innovation is intended to treat specifically identified patient conditions such as unilateral radiculopathy, neck pain, arm pain and postural abnormalities such as scoliosis.

Figure 2:
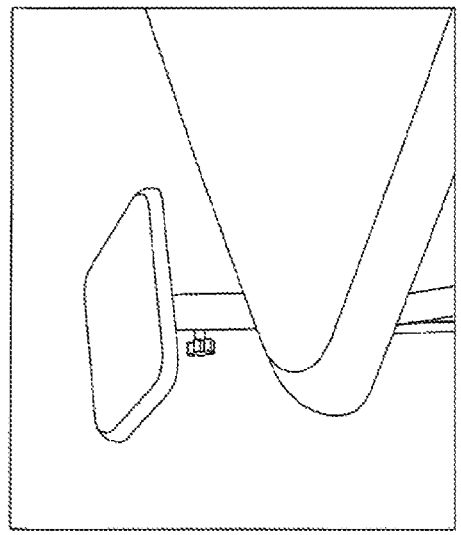
FIG. 2 is a perspective view focusing on the traction machine platform at the foot of the table, with it being shown in a first position.
Figure 3:
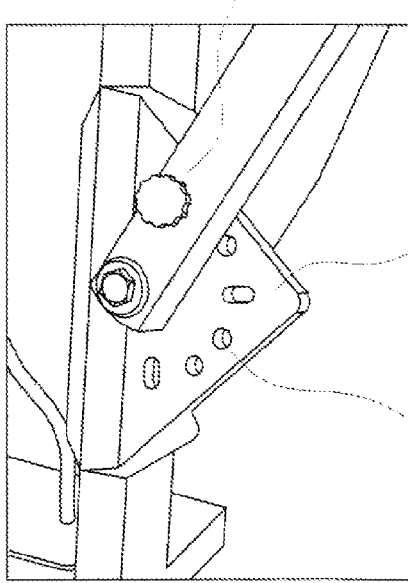
FIG. 3 is the perspective view of the traction machine platform of FIG. 2, with it being shown after being moved into a second position.
Figure 4A:
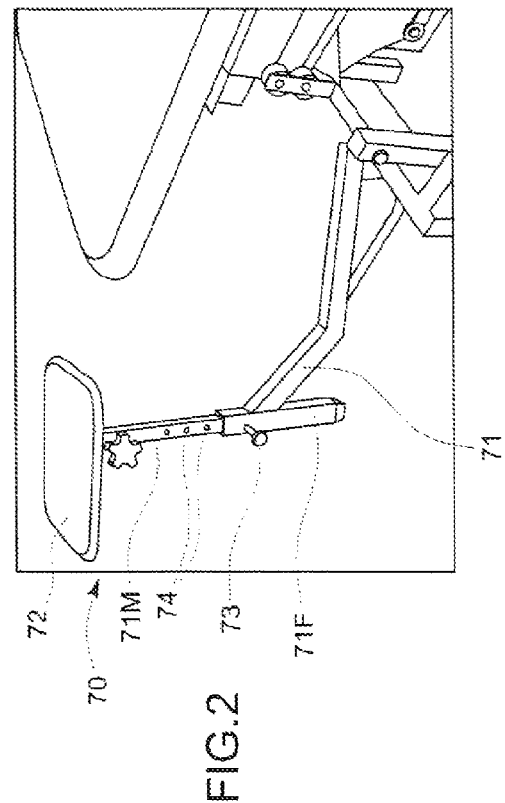
FIG. 4A is the platform arm of FIG. 2 with it capability of being rotation laterally into multiple different positions using a first embodiment of a plate and tension knob.
Figure 4B:
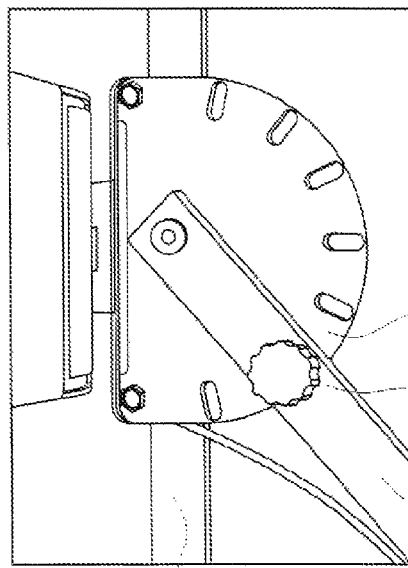
FIG. 4B is the platform arm of FIG. 2 with it capability of being rotation laterally into multiple different positions using a second embodiment of a plate and a spring biased locking pin.

The traction platform 70 (FIGS. 1A and 2) may comprise a curved or bent arm 71 that may be pivotally attached to the table frame 50 at the end of the frame being opposite to that which the cervical section 80 is mounted. The free end of the arm 71 may comprise a tube-like member 71F having a circular, rectangular, or other cross-sectional shape. A female opening in member 71F may slidably receive a corresponding male-shaped member 71M upon which is mounted a platform member 72. The height of the platform member 72 relative to the table is adjustable through a locking pin 73 in the member 71F being received in one of a series of holes 74 in the male-shaped member 71M. The traction platform 70 may be laterally adjustable, relative to a centerline running along the axial length of the table, using either a tension knob 75 on the arm 71 of the platform, and being securable to a plate 24Pi that is attached to the cross-member 24 of the base frame 20 (FIG. 4A), or using a locking pin 76 on the platform being received in one of a plurality of holes 24Ph in the plate 24Pii (FIG. 4B). This lateral and vertical adjustability in the traction platform 70 may provide a suitable platform to hold a traction machine at a convenient location to thereby apply traction to the patient.

Figure 9:
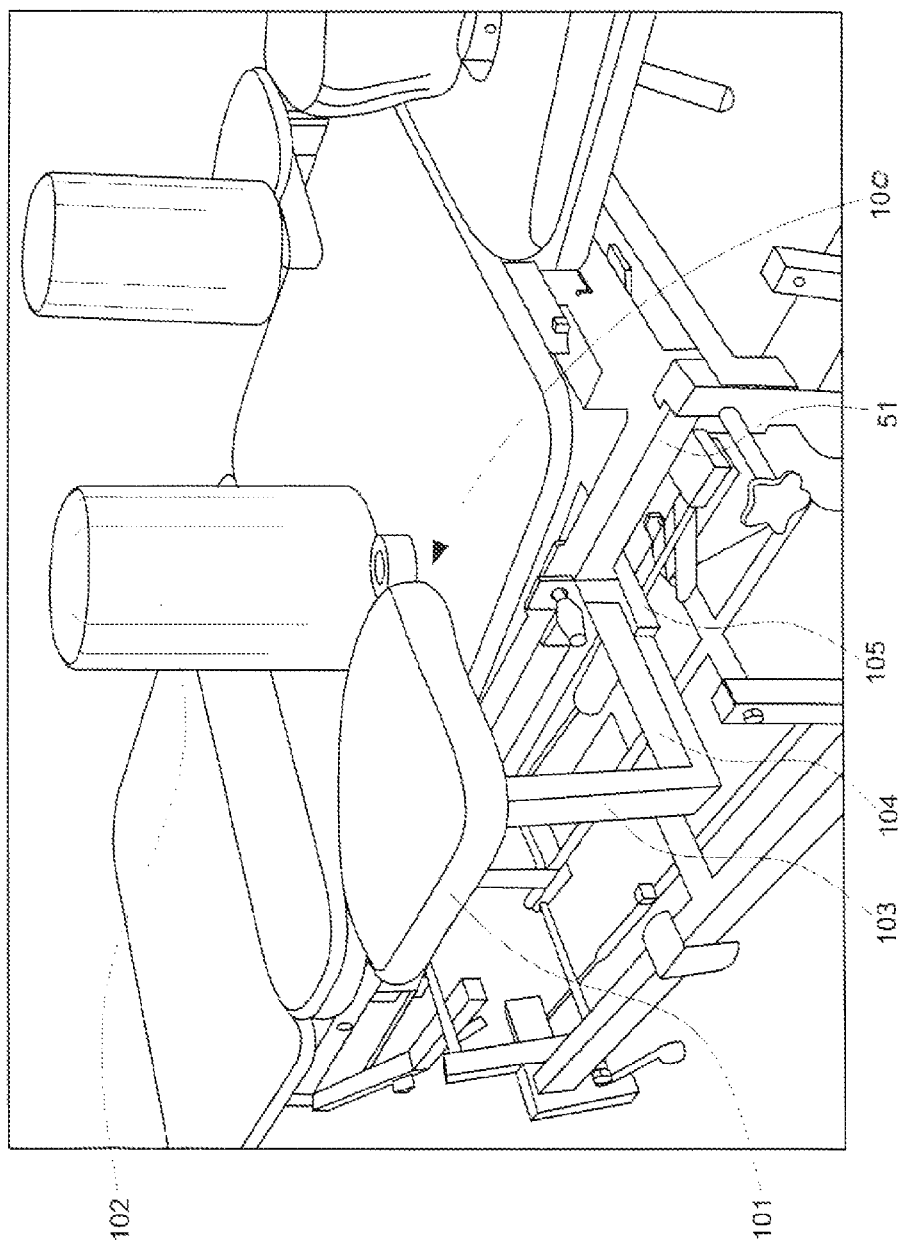
FIG. 9 is an enlarged perspective view of the multi-function treatment table of FIG. 1, showing features of the bolstering and aim rest system.
Figure 9A:
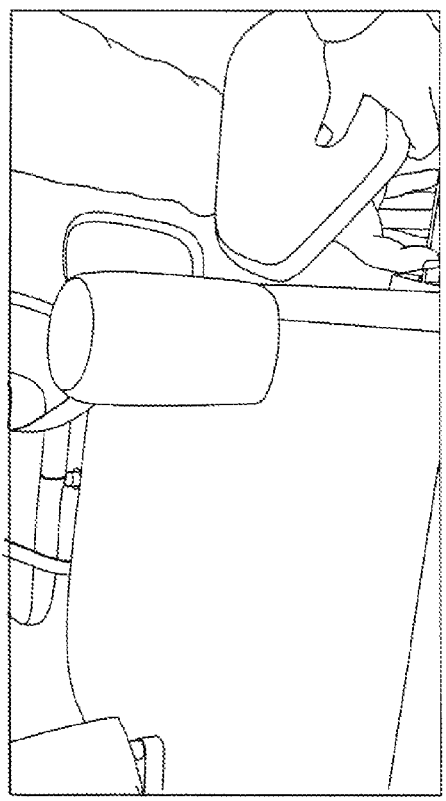
FIG. 9A is the bolstering and arm rest system of FIG. 9 having been adjusted to be in a position more distal from a patient's head.
Figure 9B:
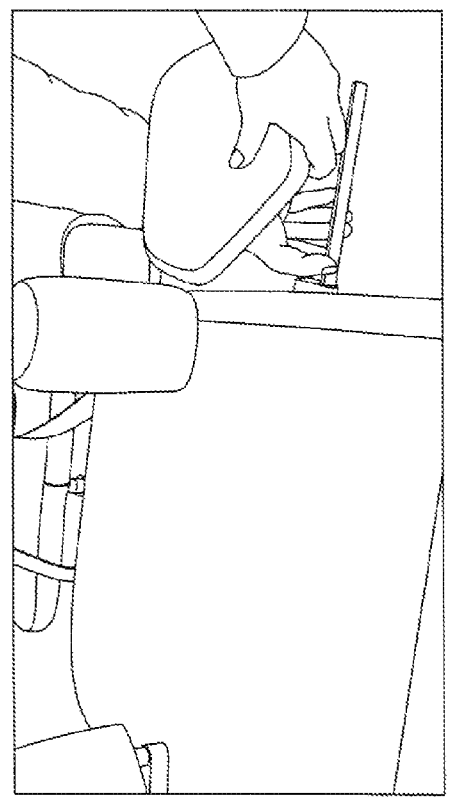
FIG. 9B is the bolstering and arm rest system of FIG. 9 having been adjusted to be in a position more proximal to a patient's head.
Figure 10:
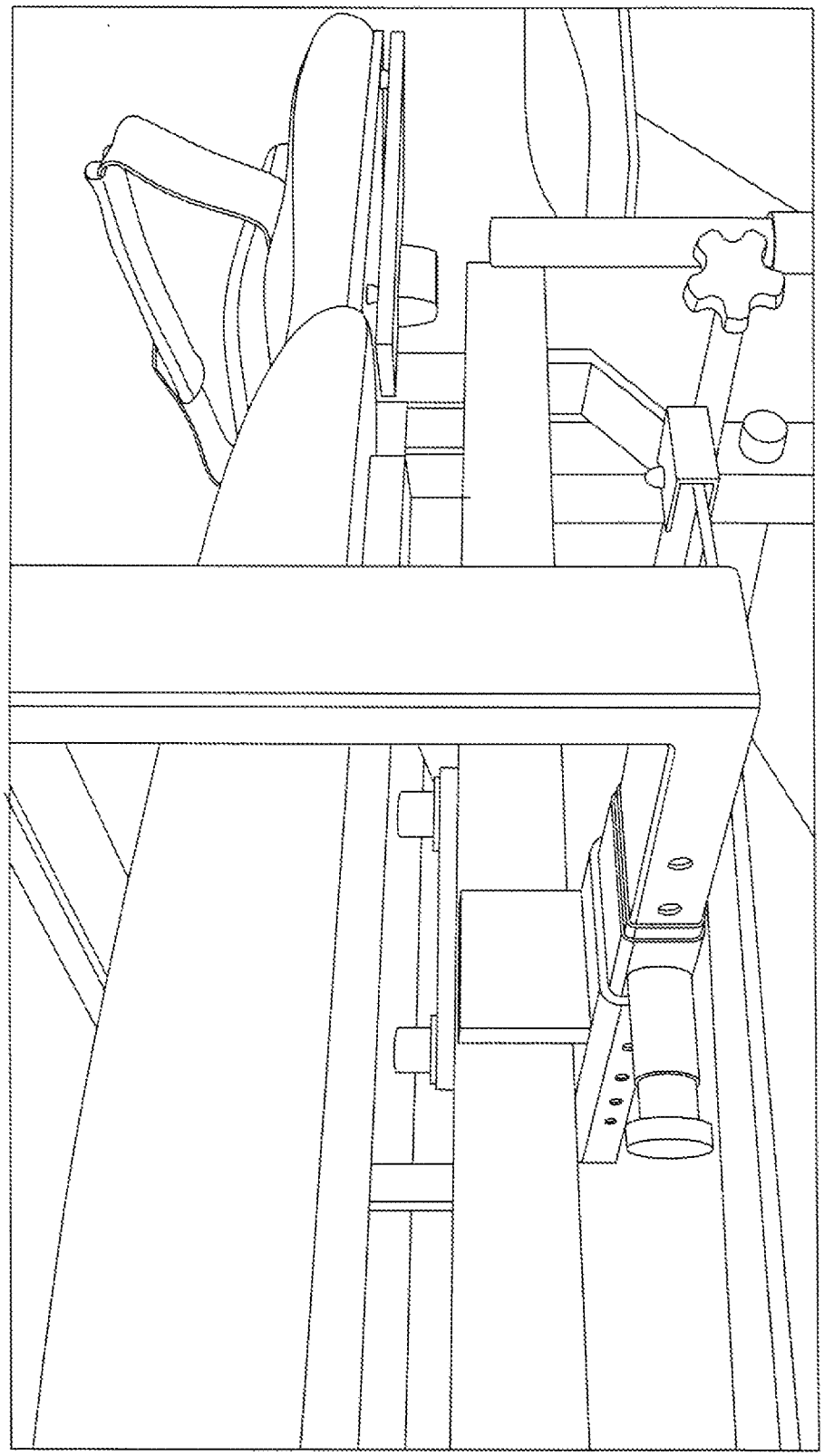
FIG. 10 is a side perspective view of the bolstering and arm rest system of FIG. 9.

The table 10 may also include an adjustable arm rest system 100 (FIG. 9). It is designed with a padded arm support platform 101, from which a cylindrical arm bolster 102 may protrude upward therefrom. The arm support platform 101 may accommodate vertical height adjustments through its attachment to male/female members similar to the vertical adjustability of the traction platform 70. The vertical support member 103 for the arm support platform 101 may be fixed to a horizontal member 104. Horizontal member 104 may be slidably received in a bracket 105 that is itself slidably mounted to the side member 51 of table frame 50. This permits adjustment of the underarm bolster system both cephalically and caudally (toward the head and toward the foot—FIGS. 9A-9B) to account for different patient heights, as well as adjustments medially and laterally (FIG. 10). The adjustment may preferably be in 1 inch increments to account for different patient widths, through the use, again, of spring biased locking pins. The armrests may adjust sufficiently for supine patient positioning to widen so as to make it comfortable and suitable for treatments where arms outstretched is a desired positioning (acupuncture, massage therapy postures, spinal decompression postures).

Each of the body support sections—chest section 60, lumbar section 61, and leg section 62—may be split into a fixed lower portion and a removable upper padded portion, where the removable upper padded portion may be replaceable with a treatment module being secured in an opening in the fixed lower section. Alternatively any of the chest, lumbar and leg sections may be integrally formed, or the body support may comprise a single table member. One example of the treatment module may comprise hot and cold compresses, which may be traditional hot and cold compresses (hot water or ice) or may comprise electrically powered heating and cooling.

Another treatment module may comprise a laser for laser therapy in treating skin conditions, and/or joint or spinal problems. As an example, an enhanced spinal decompression apparatus 110 is disclosed for non-surgical spinal decompression that combines the benefits of vertical and lateral traction, and enhanced laser treatment protocols to treat soft tissue damage and herniated disks. The laser enhanced spinal decompression apparatus 110 may comprise a first linear actuator 111 and a second linear actuator 112 (FIG. 12A) being usable to position a laser along an X direction and along a Y direction, wherein the laser and the first and second linear actuators are mounted within a box 114 (FIG. 13). The laser and associated equipment may all be contained within the metal enclosure of box 114 to prevent light from escaping and to protect against accidental damage to the equipment.

There are many different types of linear actuators, any one of which may be suitably adapted for use within the enclosure 114 to drive the laser. There are mechanical actuator types, such as ball & screw (worm gear drive shaft); wheel and axle; hoist; winch; rack & pinion; chain drive; belt drive; and cam-types, as well as hydraulic actuator types, pneumatic actuators, piezoelectric actuators, and electro-mechanical actuators. To be exemplary, the linear actuators picture herein comprise worm-drive type actuators with a stepper motor.

Figure 12A:
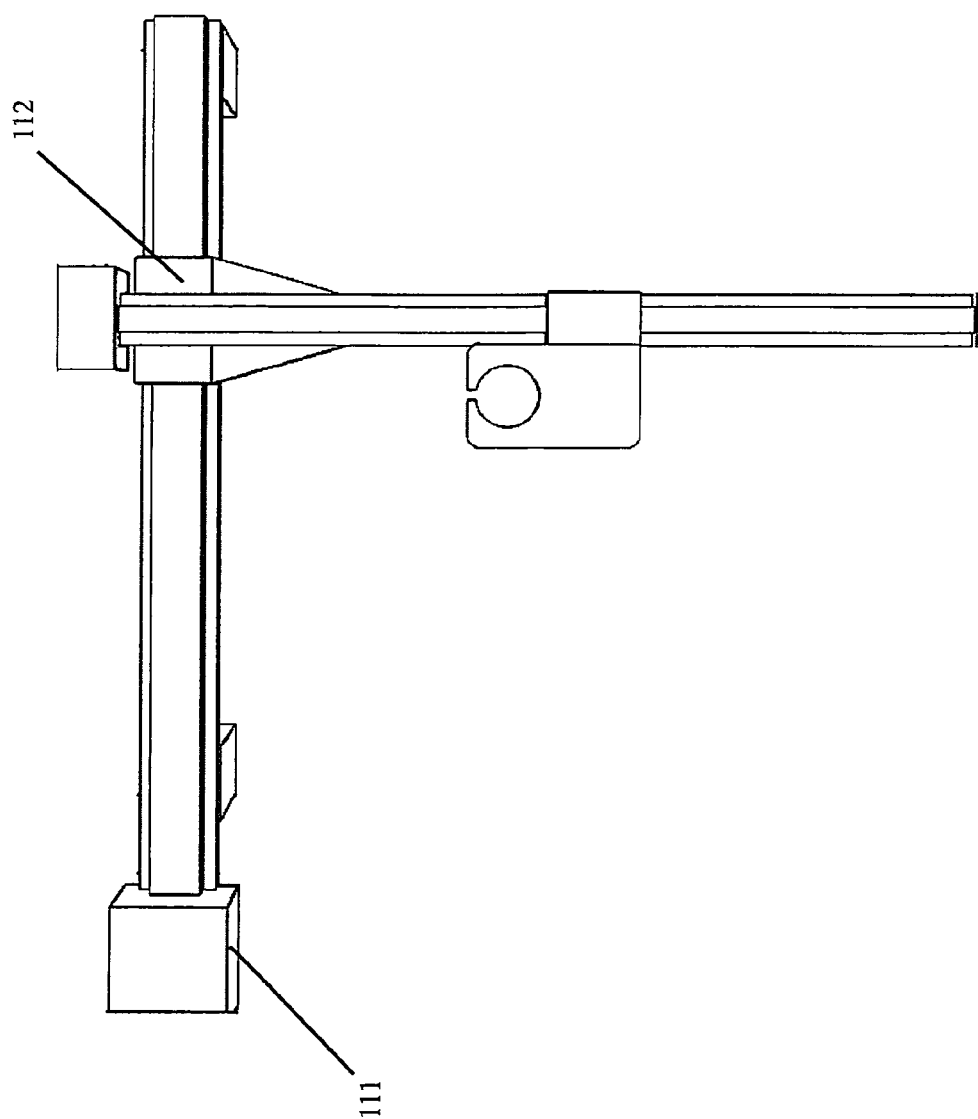
FIG. 12A is a front perspective view showing partial assembly of two linear actuators that are used to create "X" and "Y" motion to position a laser during Laser Enhanced Spinal Treatment.
Figure 12B:
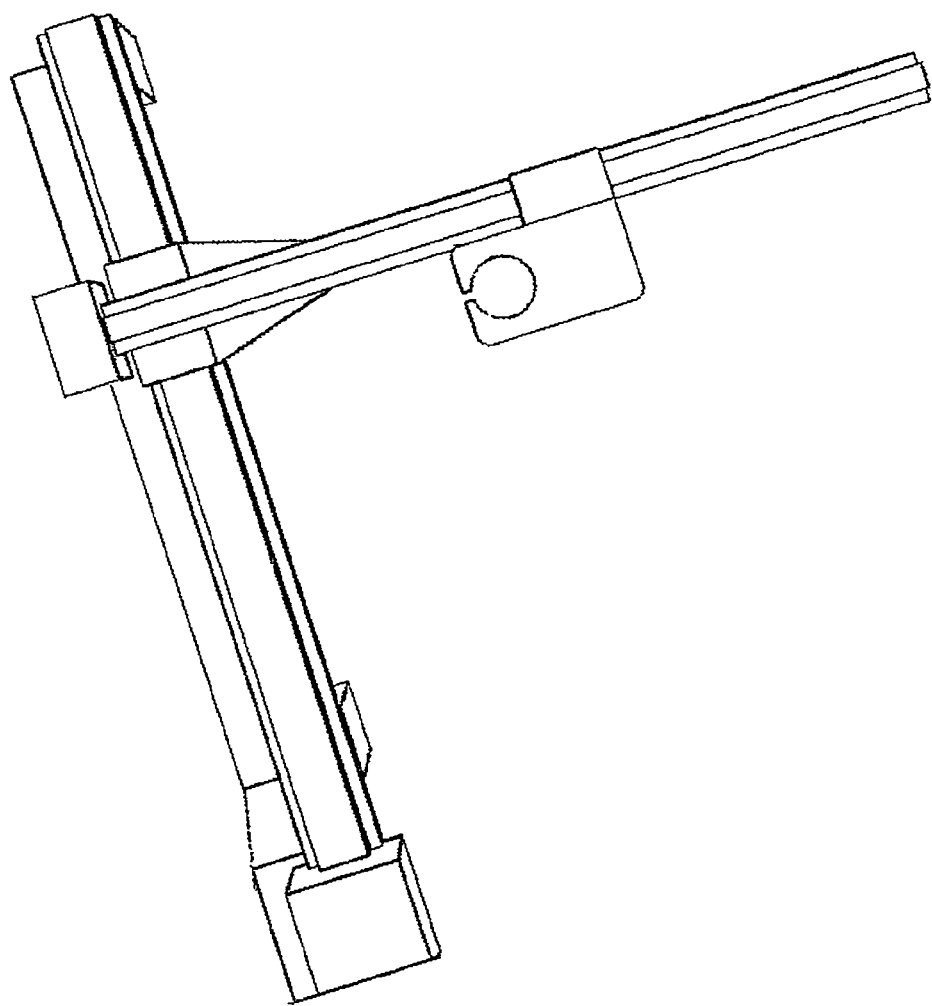
FIG. 12B is a side perspective view of the partial assembly of FIG. 12A.
Figure 13A:
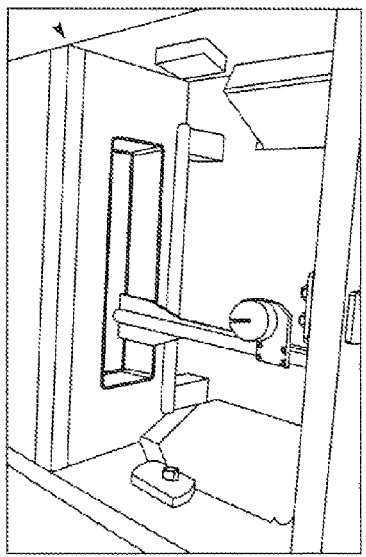
FIG. 13A is a side perspective view of the two assembled linear actuators of FIG. 12A, after being mounted in the laser automation box/enclosure.
Figure 13B:
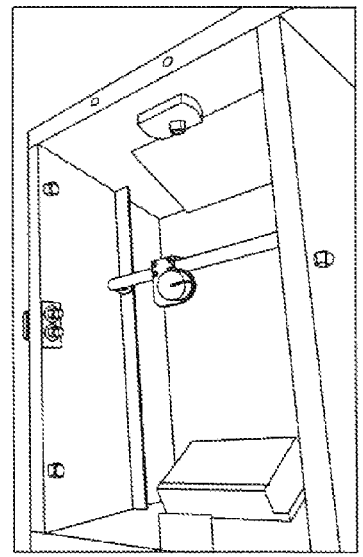
FIG. 13B is a reverse side perspective view of the laser automation box/enclosure of FIG. 12A.
Figure 13C:
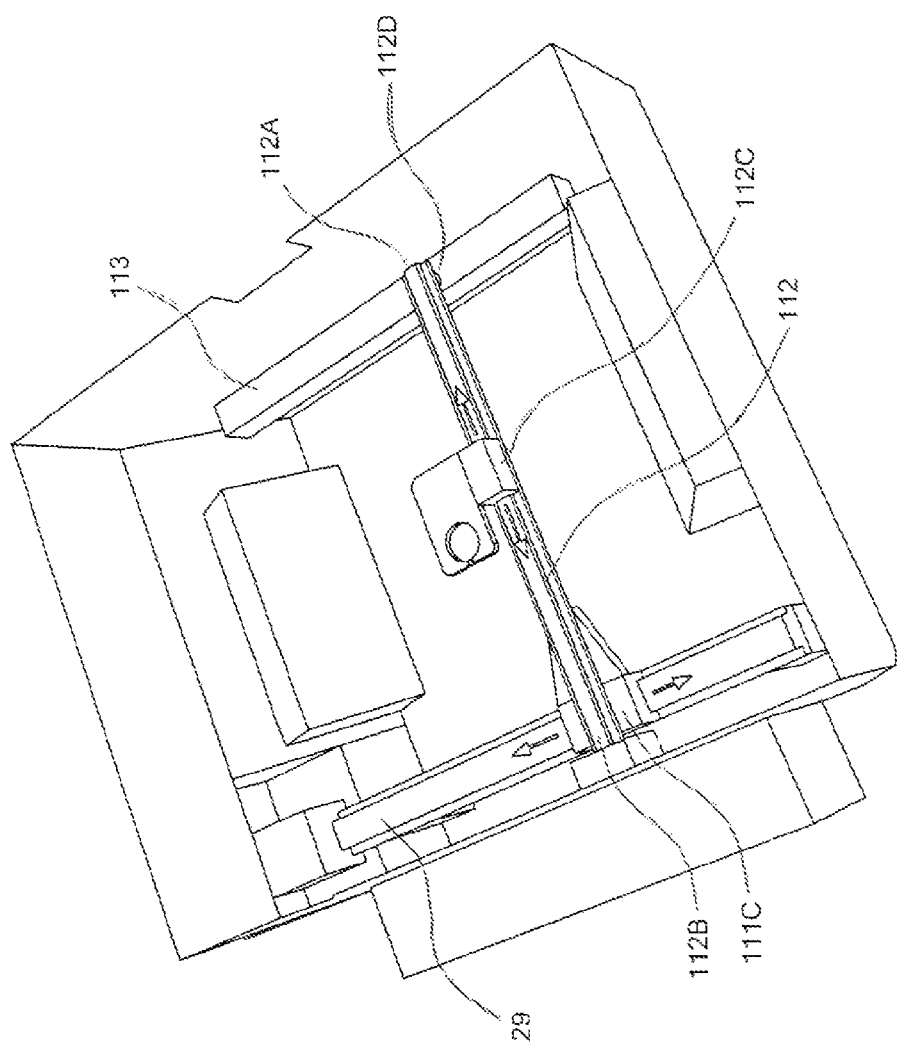
FIG. 13C is an angled perspective view of the laser automation box/enclosure of FIG. 12A.

FIGS. 12A and 12B illustrate the two worm drive actuators sitting on a fixture prior to installation within the enclosure box 114, and being oriented orthogonally with respect to each other. FIGS. 13A and 13B show side perspective views of the actuators after installation within the enclosure box 114, which is mounted to the treatment table frame. FIG. 13C shows an angled perspective view into the box 114, where a metal plate is secured to a member known as a "car" or "carriage" 112C, and which is driven by the Y-axis worm drive actuator boom 112, and is thereby drivable in the positive/negative Y directions. The second end 112B of the Y-axis worm drive actuator boom 112 may be secured to the "carriage" 111C of the X-drive actuator 111, which, when actuated, may thereby cause the Y-axis worm drive actuator boom 112 to translate in the positive/negative X directions. A first end 112A of the Y-axis worm drive actuator boom 112 may have a plastic interface part secured thereto, which may be a disk 112D that may be made of a crystalline plastic known as Delrin®, and which may travel along a fixed beam 113 that is secured to a sidewall of the box 114. This arrangement permits the first end of the Y-axis worm drive actuator boom 112 to smoothly glide along the beam and offer support to the boom, without resulting in excessive friction.

Figure 13D:
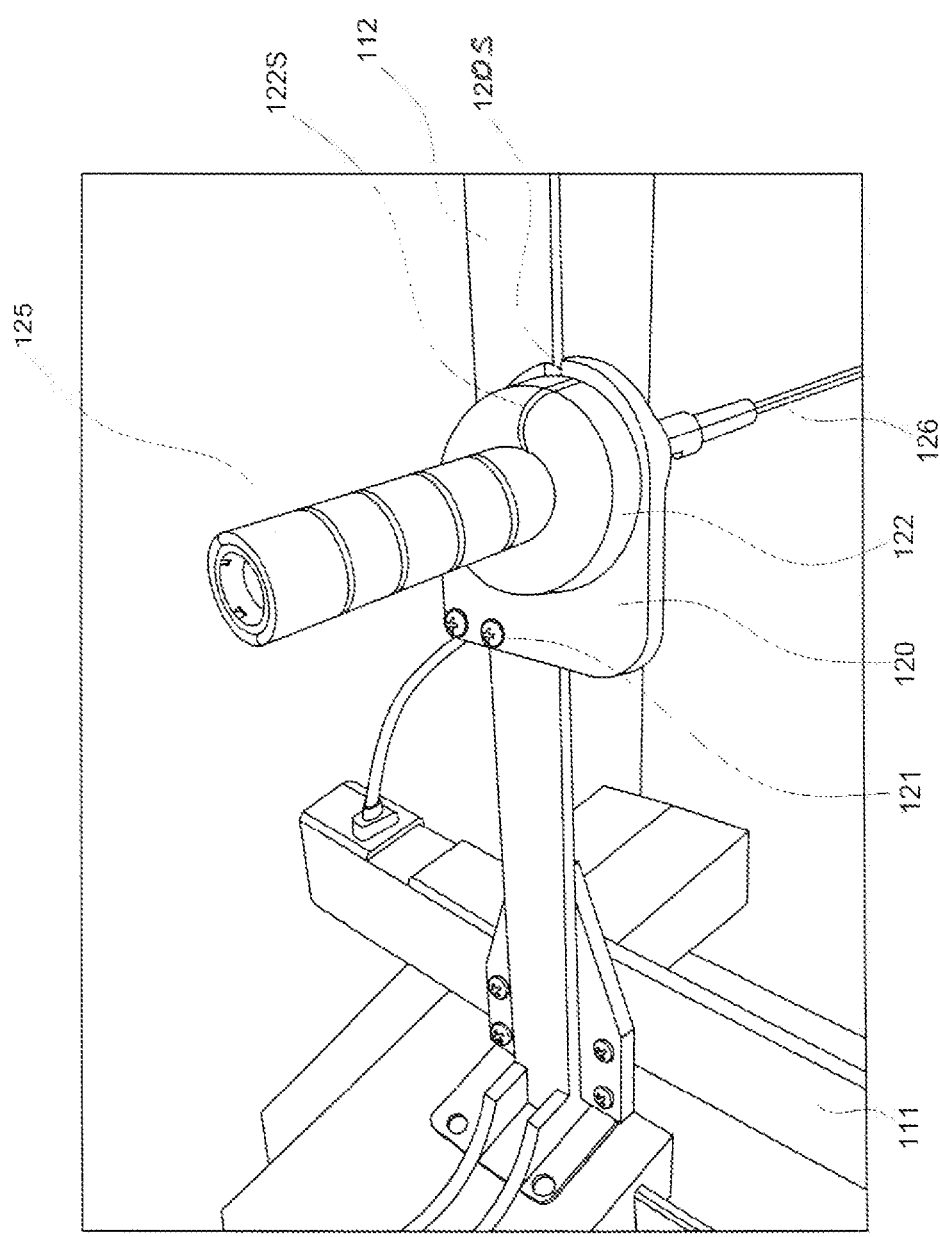
FIG. 13D is an enlarged view of the laser hand-piece of the current invention being releasably received into the corresponding retaining ring that is secured to an aluminum tray attached to the X-axis linear actuator.

As seen in FIG. 13D, the Y-axis worm drive actuator 112 may have a plate 120 secured to the actuator boom "car" 112C, which may be a metal plate that is secured using mechanical fasteners such as screws 121. The plate 120 may cantilever away from the actuator 112 to provide unrestricted support for a laser holder 122 that may releasably receive the laser hand-piece 125 with its associated fiber optic cable 126. The laser holder 122 may be cylinder-shaped member with a concave center portion to receive a corresponding shape of the laser hand-piece 125. Both the plate 120 and the laser holder 122 may have a respective slot 120S and 122S therein to accommodate the fiber optic cable 126 that connects the laser hand-piece 125 with the control module. This permits the laser hand-piece 125 to be easily seated or removed without disconnecting the cables. A detent or snap ring may be used to releasably retain the laser hand-piece 125 within the laser holder 122.

Figure 13E:
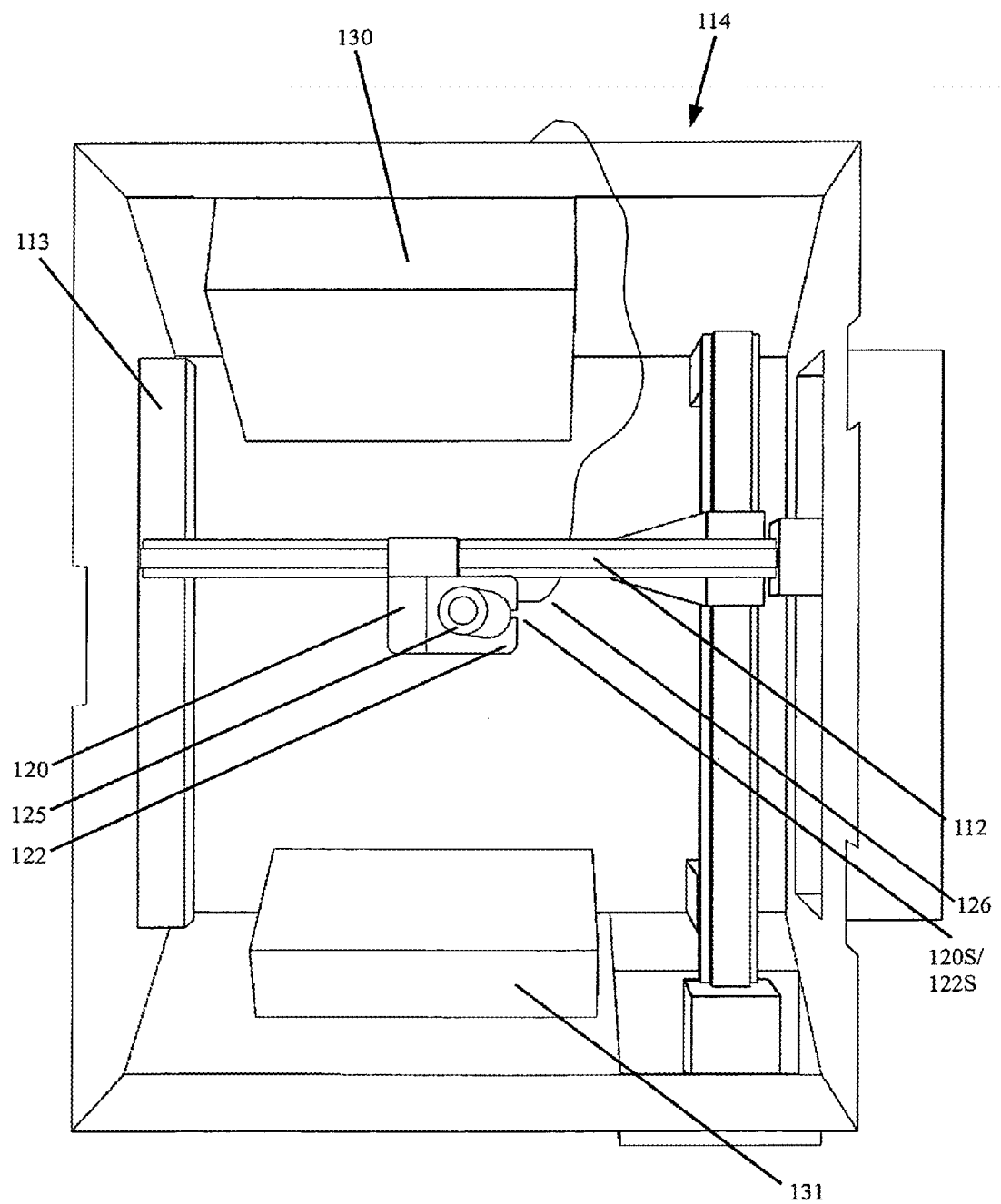
FIG. 13E is a top perspective view looking into the opening of the laser automation box/enclosure.

Each of the actuators 111 and 112 may have an encoder to determine the distance of travel by each of the respective cars, 111C and 112C, so the system may accurately determine or sense the position of the laser through the position of each car. Software for driving the lasers with the actuator cars may work in conjunction with the encoders, and may contain safety protocols that may sense an unexpected stoppage in motion, which will trigger a relay or switch to shut the system down, including power to the laser. This may serve to prevent overheating of the target area of the patient by the class 4 laser, or damage to the system. In addition, secondary position sensing may be provided at the furthest limits of travel in both directions for each of the two linear actuators the using limit switches or proximity sensors, which may serve to calibrate the system or serve as a primary system stop to prevent over travel and damage to the actuators. A hard stop may provide a backup, whereby contact of the actuator carriage with the hard stop due to failure of the encoder or sensor may result in an over-current condition that is detected by the controller. In FIG. 13E, the green colored controller circuit board 130 is positioned within the upper portion of enclosure 114, while the power supply 131 is positioned within the lower portion of the box 114, and may be protected by a metal grate.

Figure 14A:
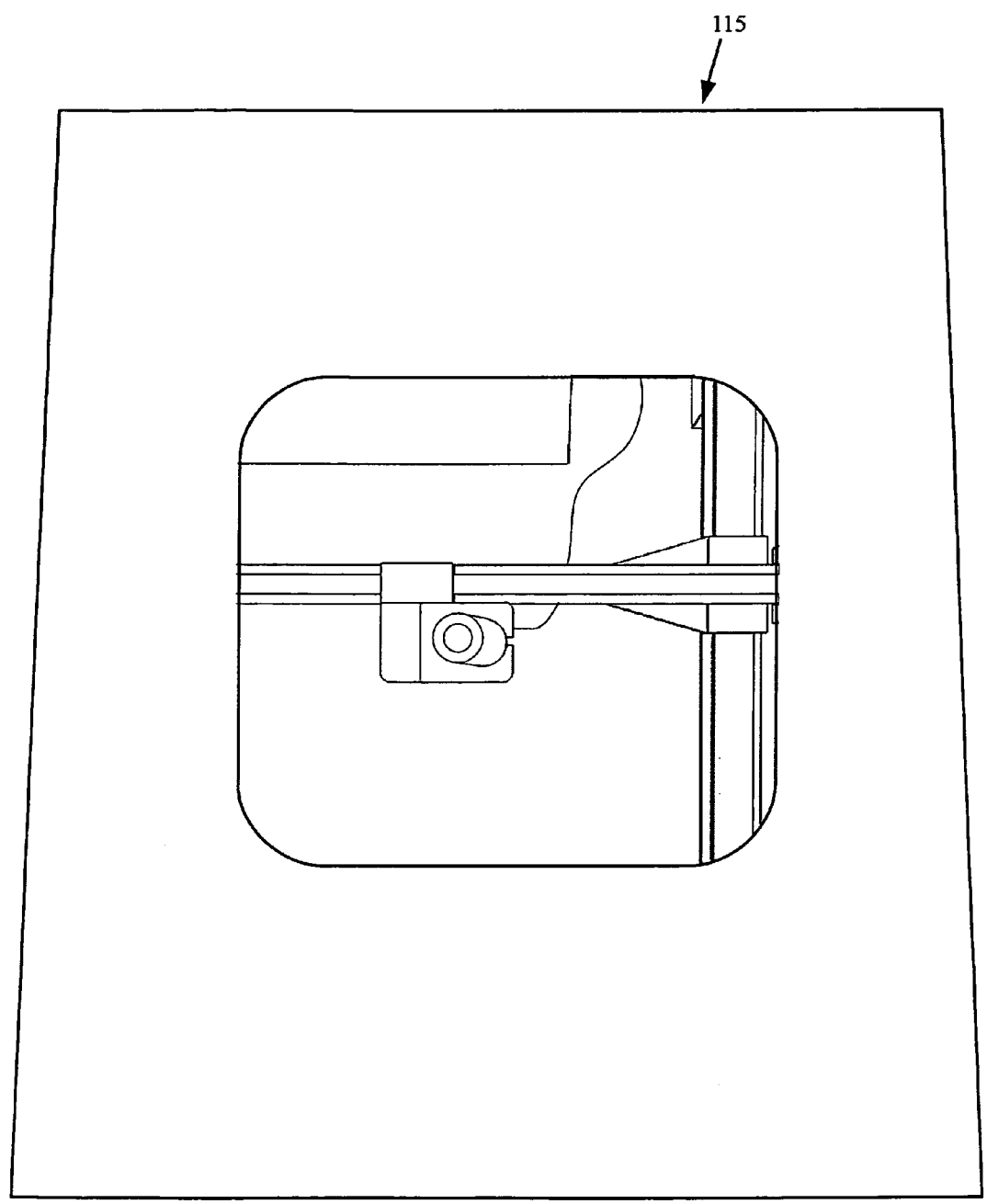
FIG. 14A is a top perspective view of the enclosure of FIG. 13E, after installation within the treatment table of the current invention, and after installing the protective cushioned gland around the perimeter of the top of the box, for sealing against a patient.
Figure 14B:
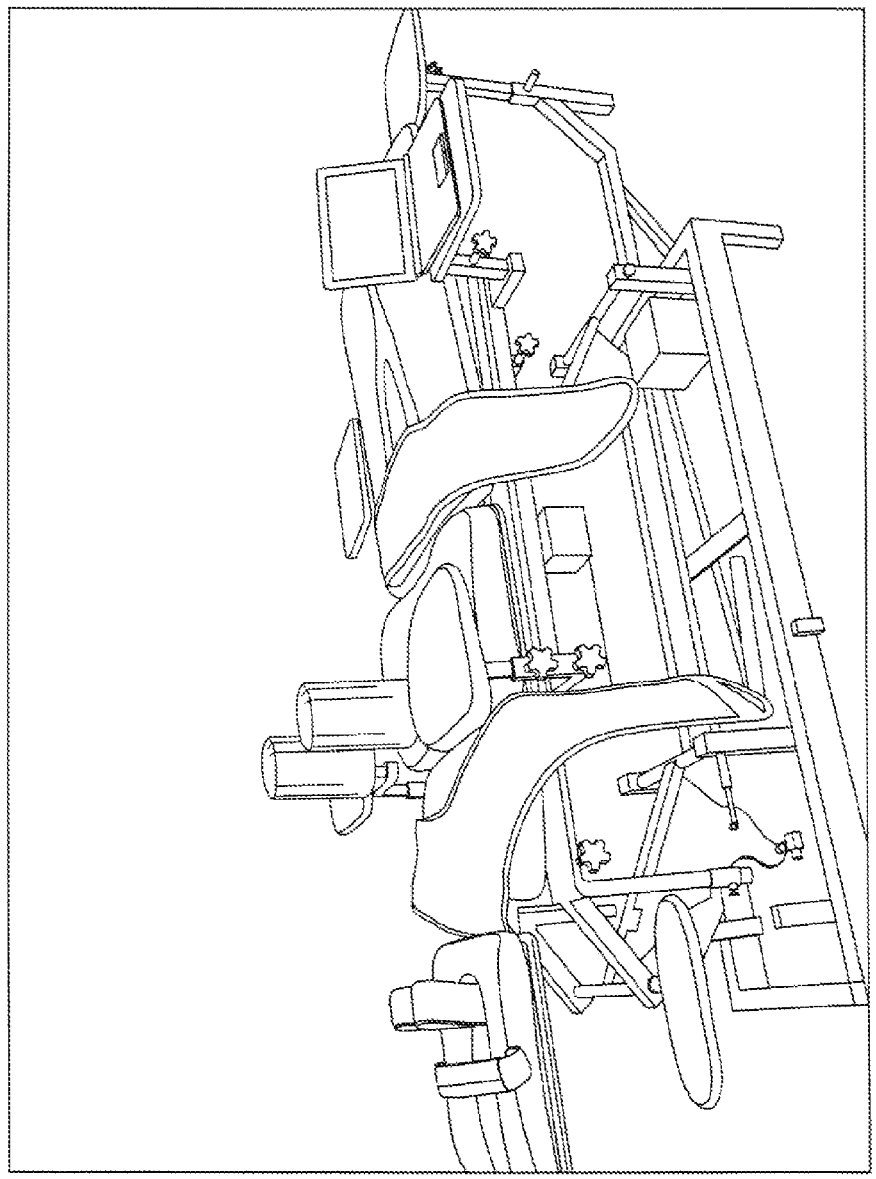
FIG. 14B is a perspective view of a treatment table of the current invention, utilizing a laser treatment module/box in a lumbar, with the electrical drive circuitry for the laser and the linear actuators being coupled to a laptop computer through a motion controller, and being responsive to instructions from software running on the computer.
Figure 14C:
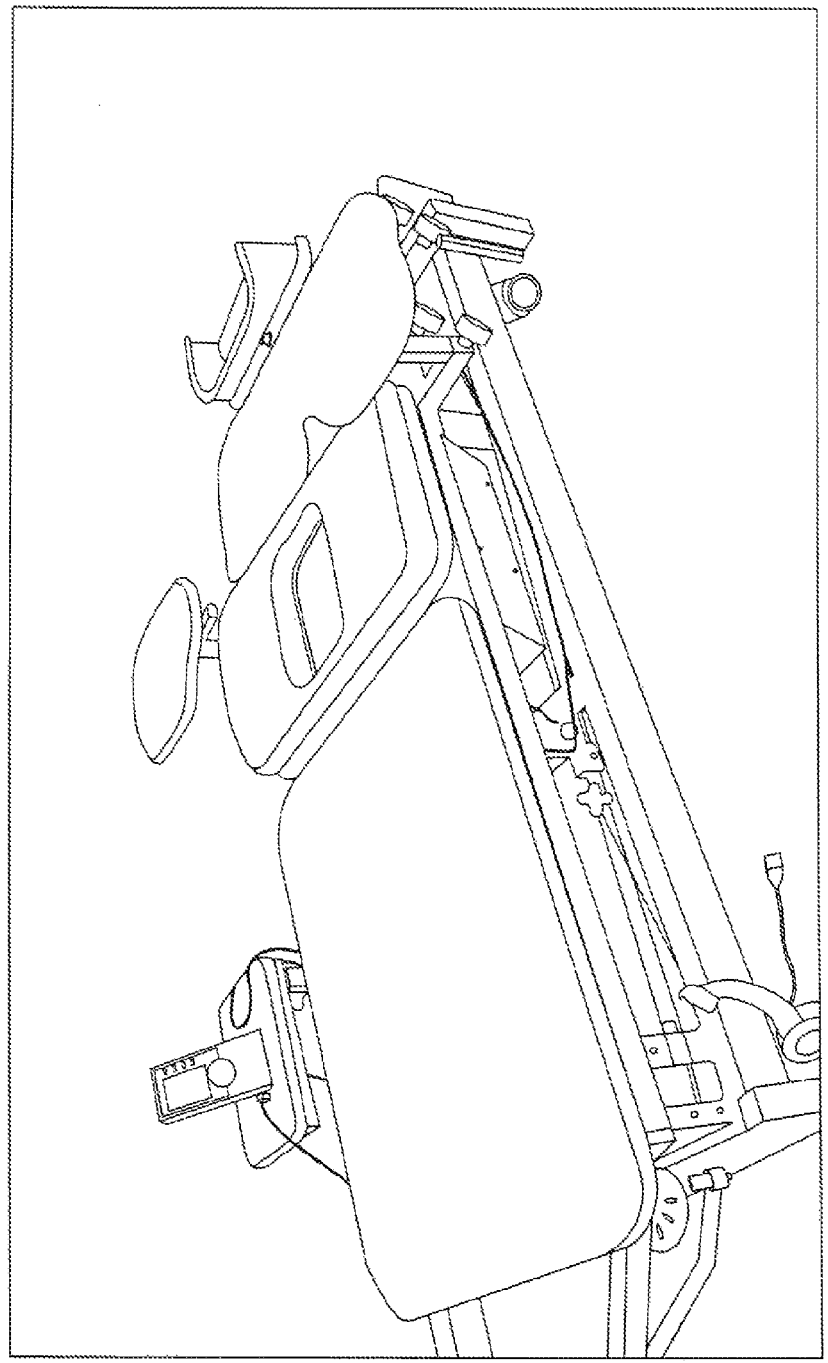
FIG. 14C is a reverse perspective view of the treatment table of FIG. 14B.

FIG. 14A shows the enclosure 114 of FIG. 13E being covered by a cushioned gland 115 around a top perimeter of the box to create a seal against a patients' skin surface to thereby prevent or reduce laser light from being transmitted about the room by escaping therefrom. Additional proximity sensors, which are known in the art, may also be used near the opening in the box 114 to detect the presence of a torso on the centre pad (over the laser box) to provide a safety shut off to the laser to avoid potential eye damage when the laser box opening is not covered during treatment being provide by the laser. The laser treatment provided by this enhanced spinal decompression apparatus may comprise the laser emitting specialized laser light upon a spine of a patient, with the laser translating in the X and Y directions and being directed to emit light according to a specific treatment protocol. The laser may emit a range of different wavelengths, however in one embodiment, a wavelength of 940 nm+/−15 nm is used, and may provide a depth of penetration on the order of approximately 5 millimeters on a low power setting for treatment of dermatological conditions and scarring, and a depth of approximately 10 cm on full power for treatment of deeper spinal and joint conditions. The laser may be capable of delivering 620 joules per minute of energy.

The laser enhanced spinal decompression apparatus may comprise the controller 130 interfacing with software to permit any number of specialized treatment protocols to be pre-programmed and/or to be customizable for individual patients. In particular, an interface application program (see screenshots in FIGS. 15A-15E) that allows a practitioner to initiate laser treatments from the screen of a PC running Windows (or alternatively initiated from an existing portable control device that mounts to a docking port on the table), may coordinate with a commercially available controller program, such as "GallilTools," which is available from Galil Motion Control of Rocklin, Calif. (see www.galilm-.com/products/galiltools.php, the disclosures of which are incorporated herein by reference).

Figure 19:
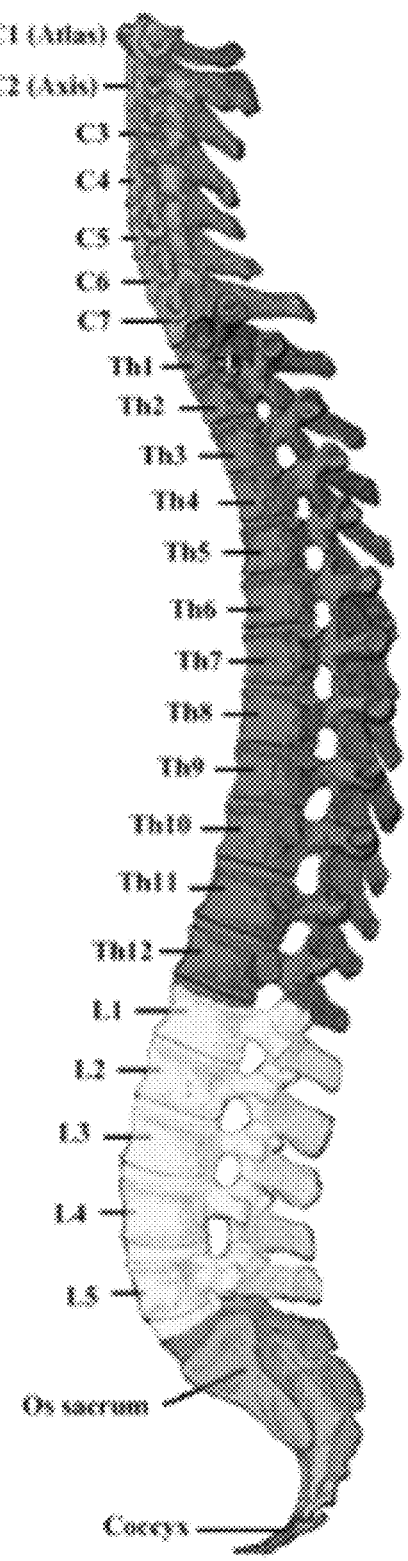
FIG. 19 is a generic illustration of the division of segments in a human spine.

The linear actuators may preferably provide the laser with a range of motion for the treatment protocol comprising travel of approximately 4 to 8 inches or even more to each side of a center of a patient's spine (or a particular joint), and a range of motion for travel up and down a patient's spine to cover spinal disks from L1 to S1 (see FIG. 19). The optimal angle for emission of the laser is, in part, controlled by the laser's specially designed lens, which diverges the beam at an optimal angle while maintaining uniform dosage intensity across the beam, and is designed by Biolase Technologies. Included is an optional mechanism by which the laser hand-piece can be automatically angled at 45 degrees to the treatment surface which can be maintained within or beyond the travel range.

The laser enhanced spinal decompression apparatus may also comprise one or more sensors, being optical sensors, temperature sensors, pressure sensors, and/or motion sensors. The sensor may provide useful data during treatment. For example, one or more temperature sensors may be used for thermographic imaging to thereby monitor tissue temperatures to achieve an optimal dosage by the laser.

Programmed Protocols for the Laser Enhanced Spinal Decompression Technique may be in one of at least two modes: a Quadrant Selection Mode and a Protocol Mode. In the quadrant selection mode, six quadrants may be treated as follows:

2 centre between approximately L3-S2 (distal) and T12-L3 (proximal)

2 right sided and 2 left sided at the same level.

Figure 14D:
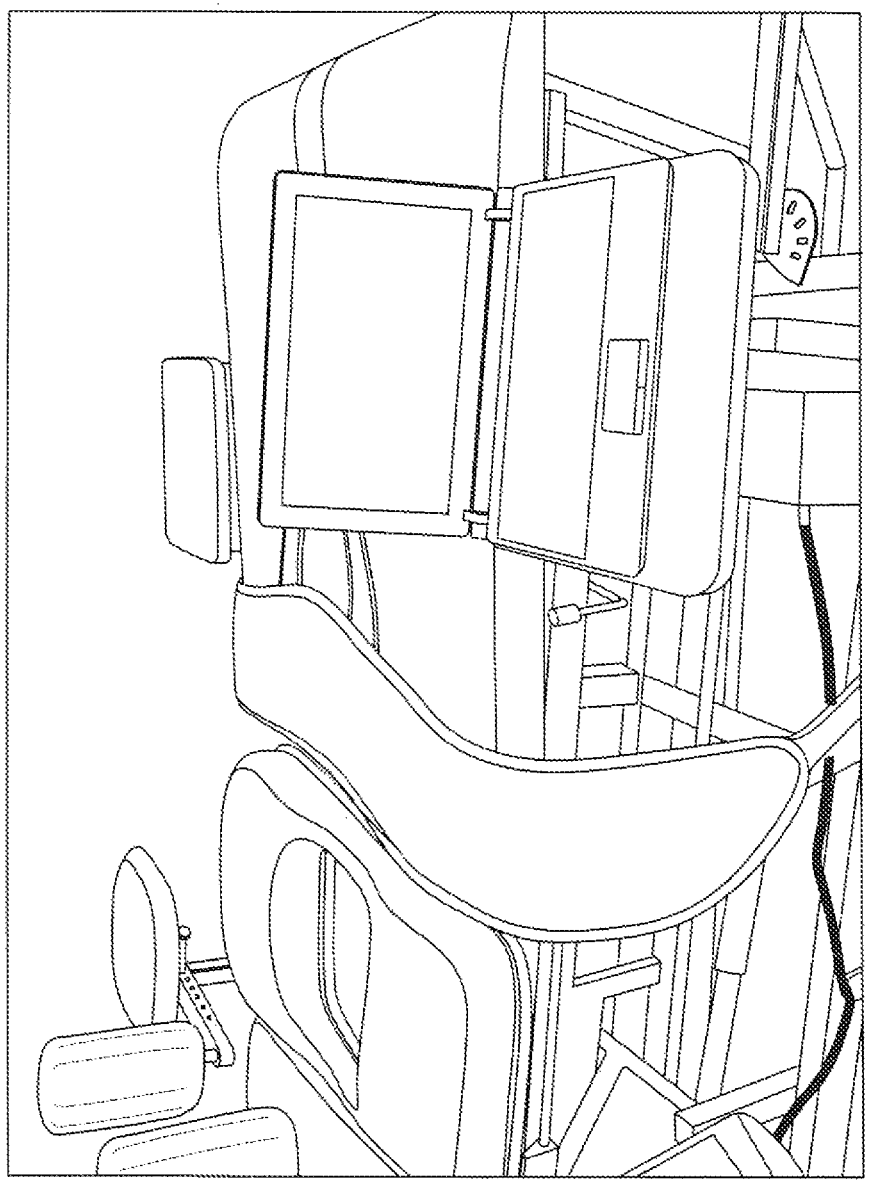
FIG. 14D is the treatment table of FIG. 14B, but enlarged to show the gland above the laser treatment module/box and the opening therein, as well as the laptop computer being coupled using a USB cable to command the treatment protocols that are performable by the module.
Figure 15A:
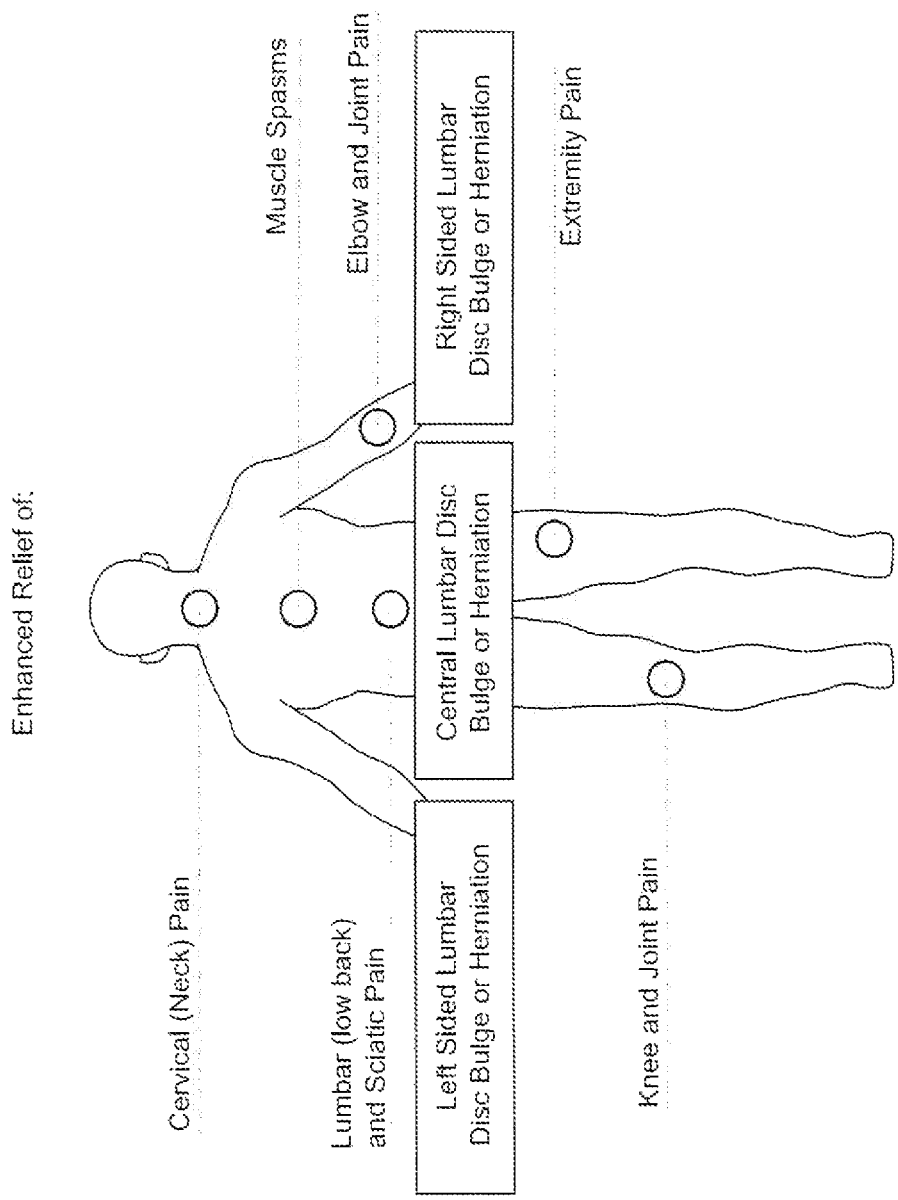
FIG. 15A is a screen shot of the software of the current invention being run on the laptop of FIG. 14B, and illustrating the various regions of the body upon which the laser may be used for treatment.
Figure 15B:
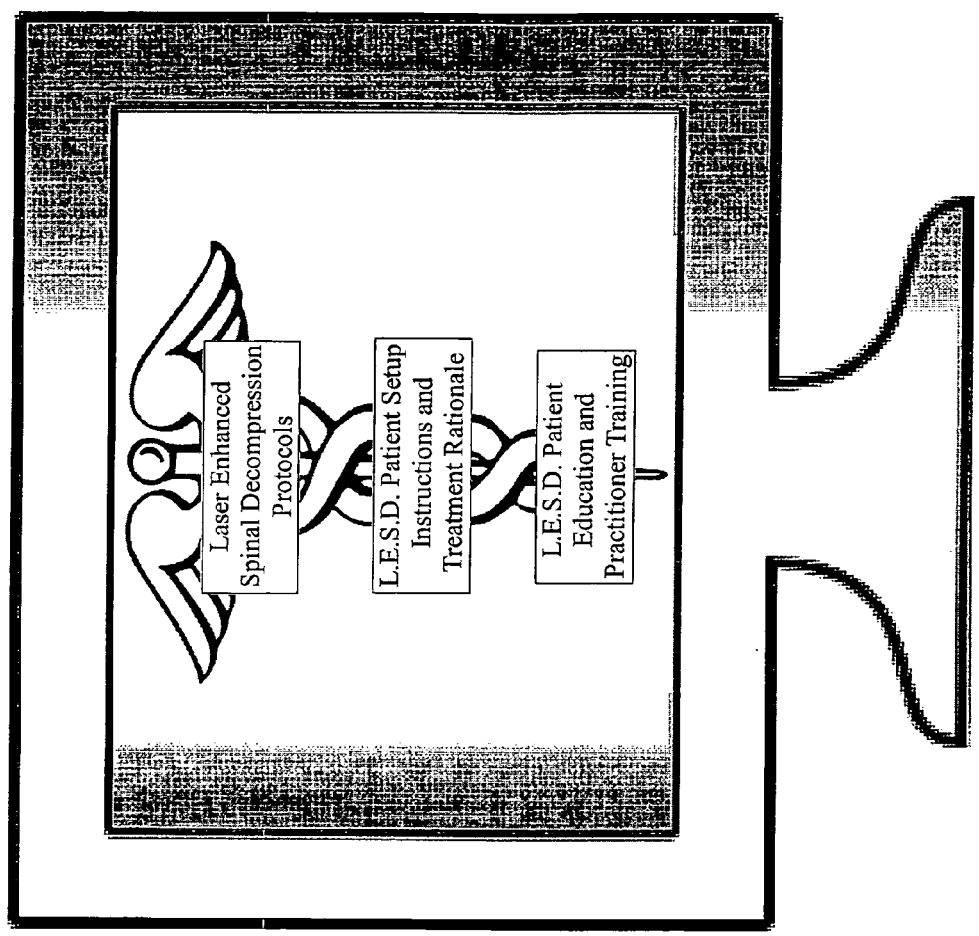
FIG. 15B is a screen shot illustrating one aspect of the software of the current invention, showing options relating to the Laser Enhanced Spinal Decompression of the current invention, including window buttons to access specific Protocols, Patient Set-up instructions, and Practitioner training options.
Figure 15C:
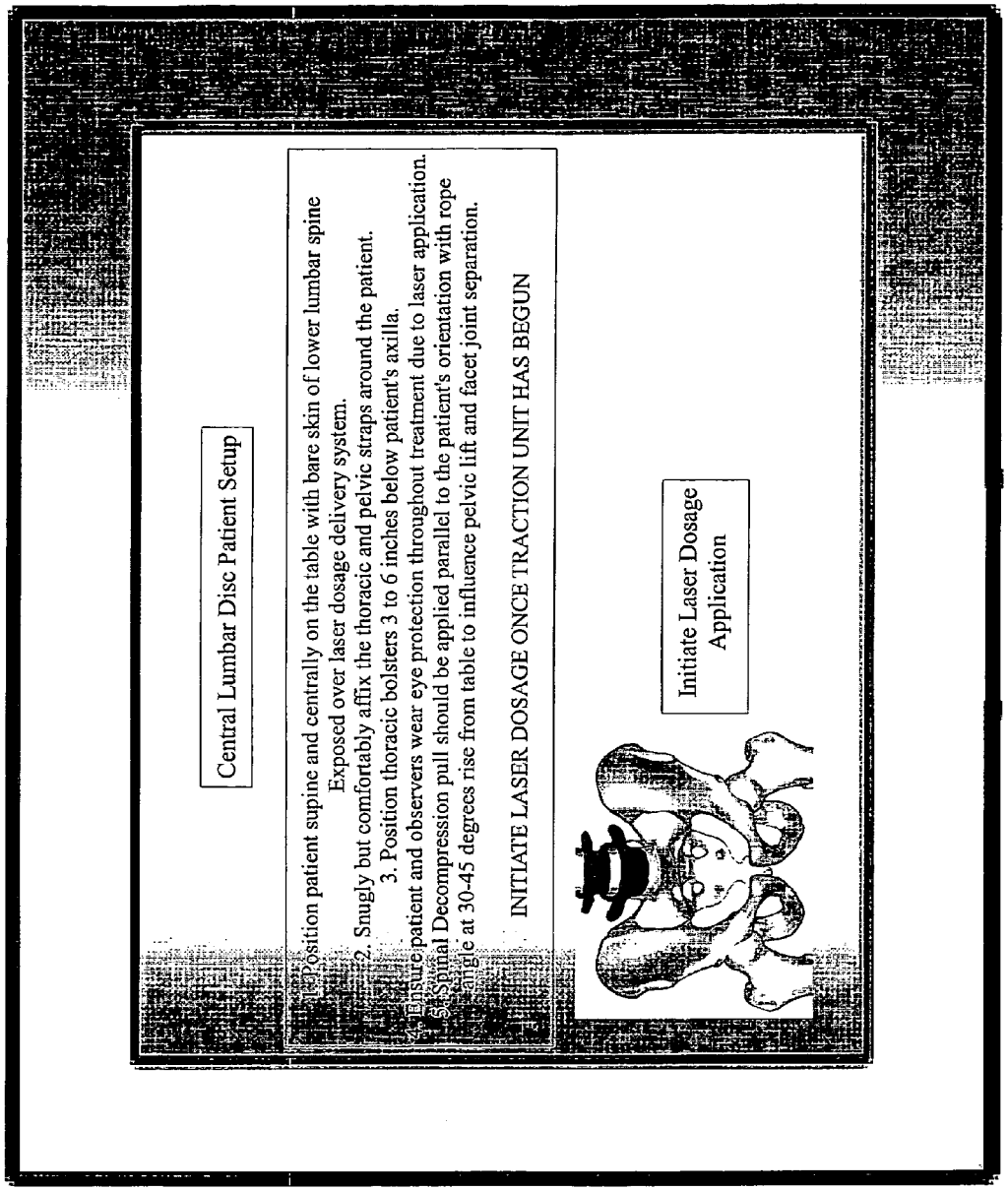
FIG. 15C is a screen shot illustrating another aspect of the software of the current invention, showing a checklist for a practitioner to follow in performing central lumbar disc Laser Treatment.
Figure 15E:
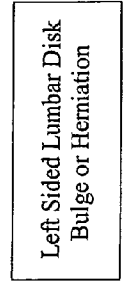
FIG. 15D-FIG. 15F are screen shots illustrating yet other aspects of the software of the current invention, showing window button options for spinal decompression therapy of central disk, right-side disk, and left-side disk regions.
Figure 15D:
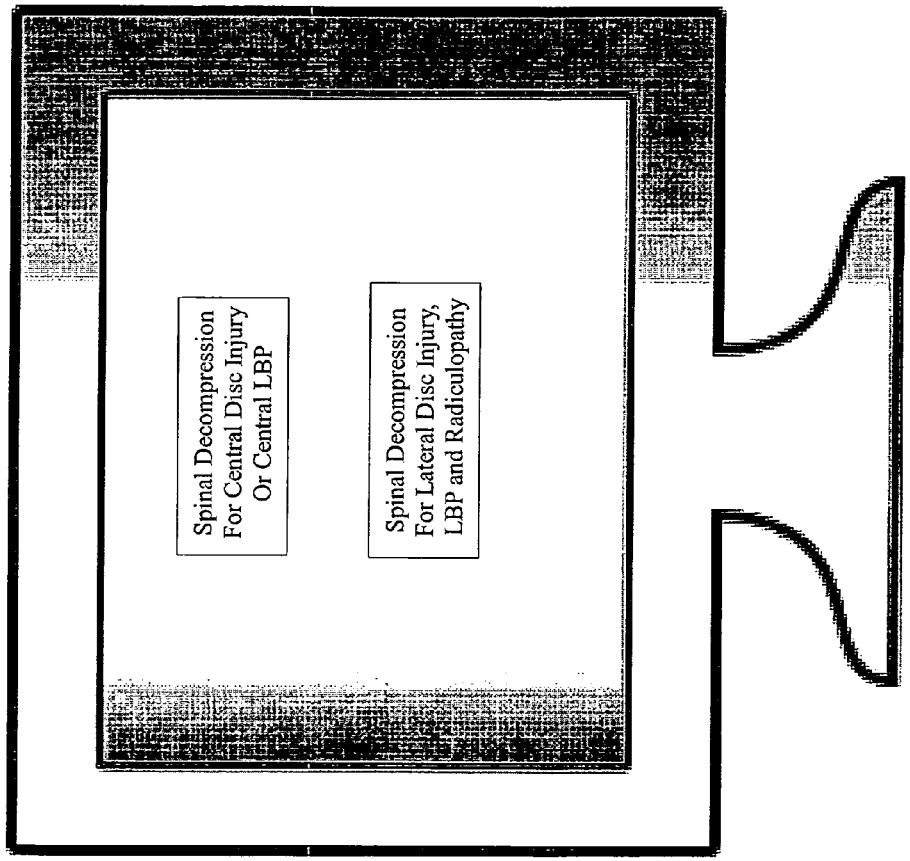
Figure 15F:
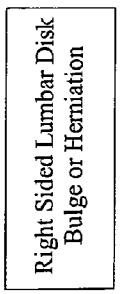
Figure 16A:
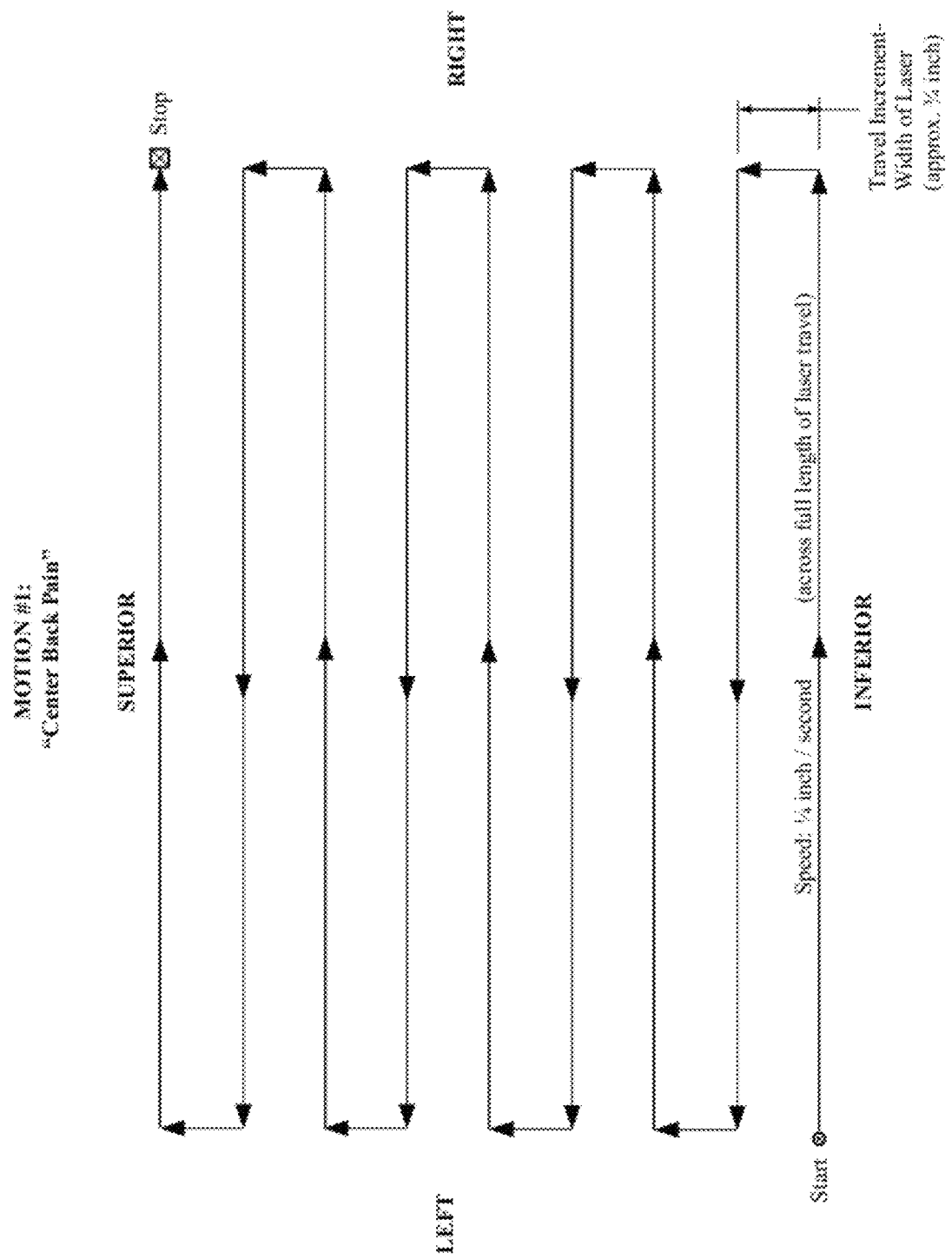
FIG. 16A-16H show drawings for the pre-programmed automated laser motion protocols for various conditions.
Figure 16B:
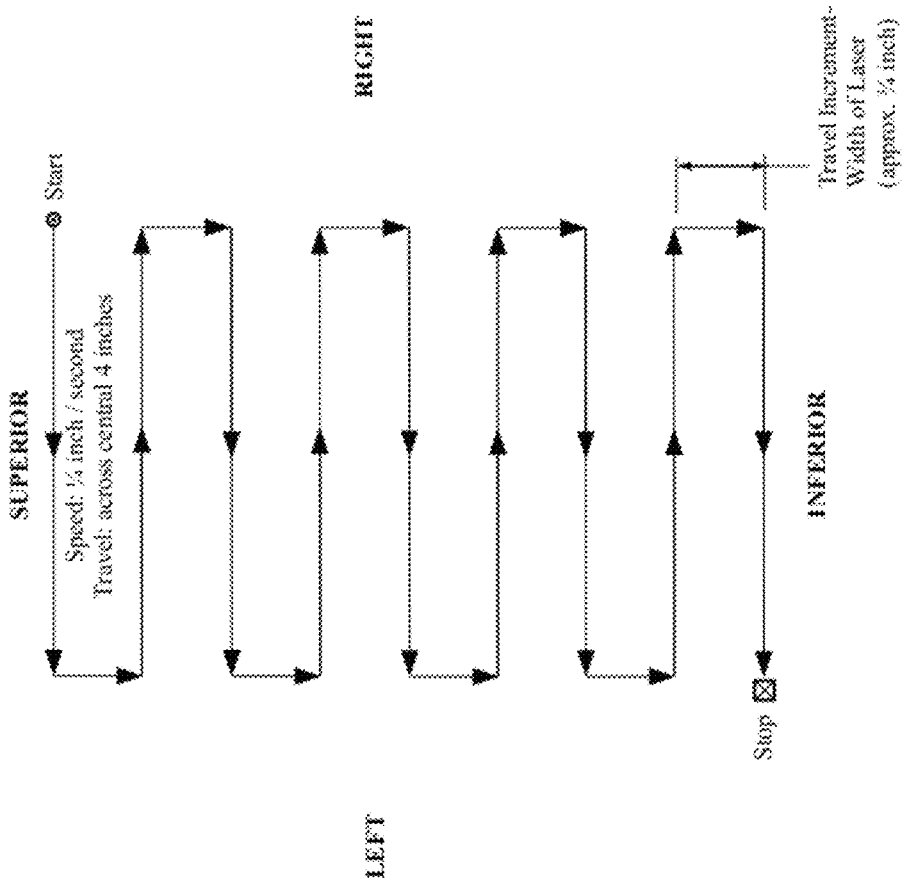
Figure 16C:
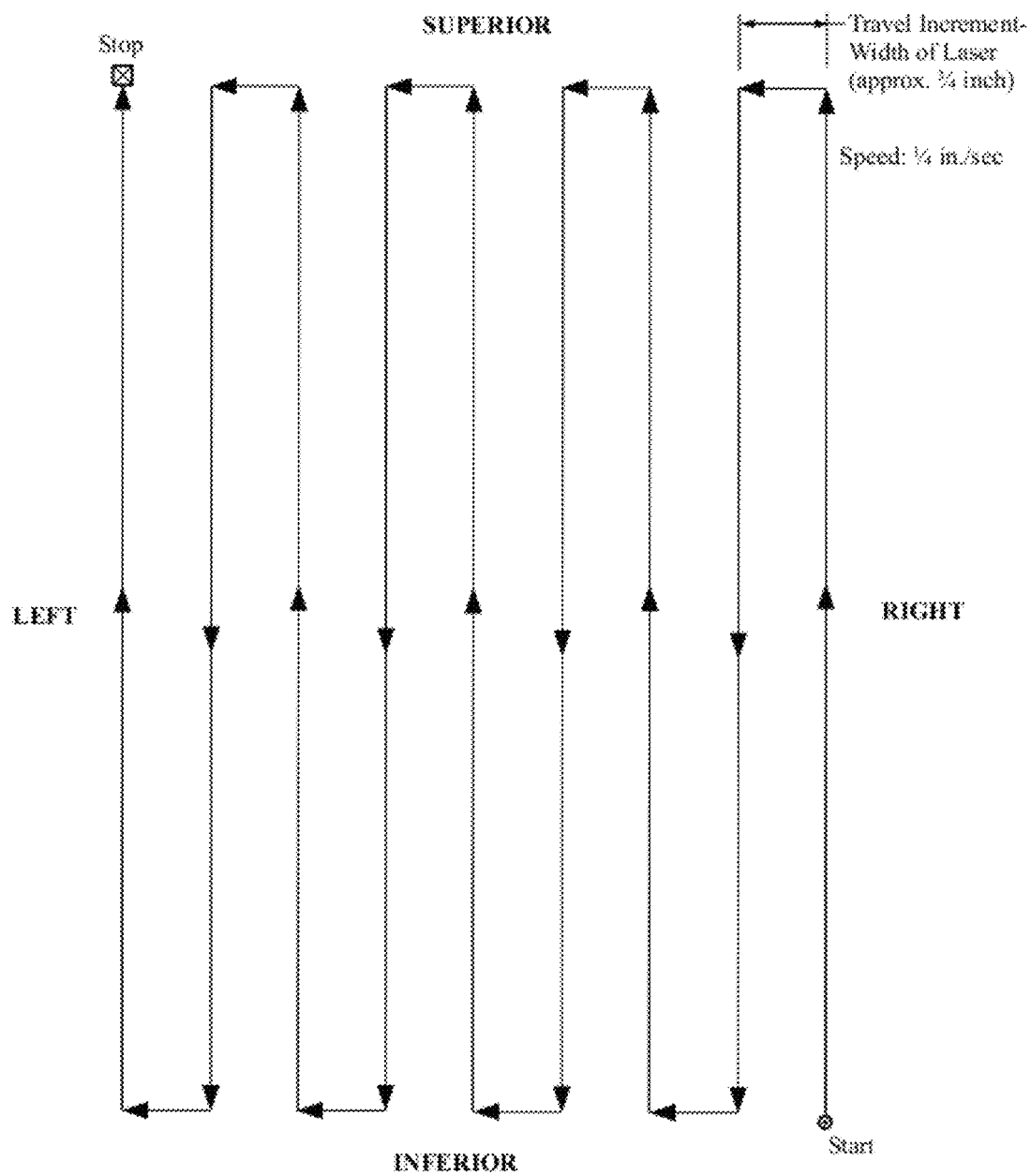
Figure 16D:
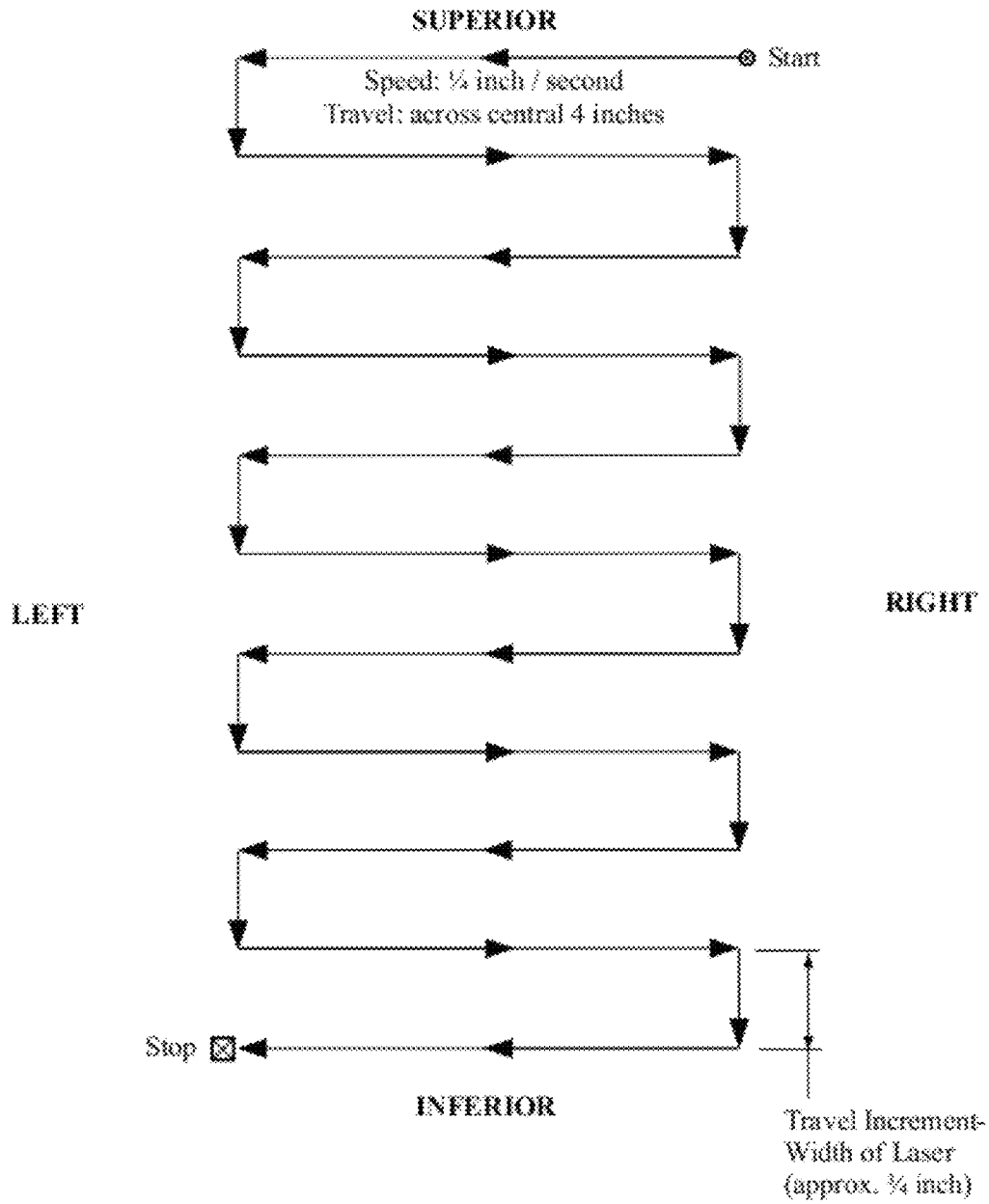
Figure 16E:
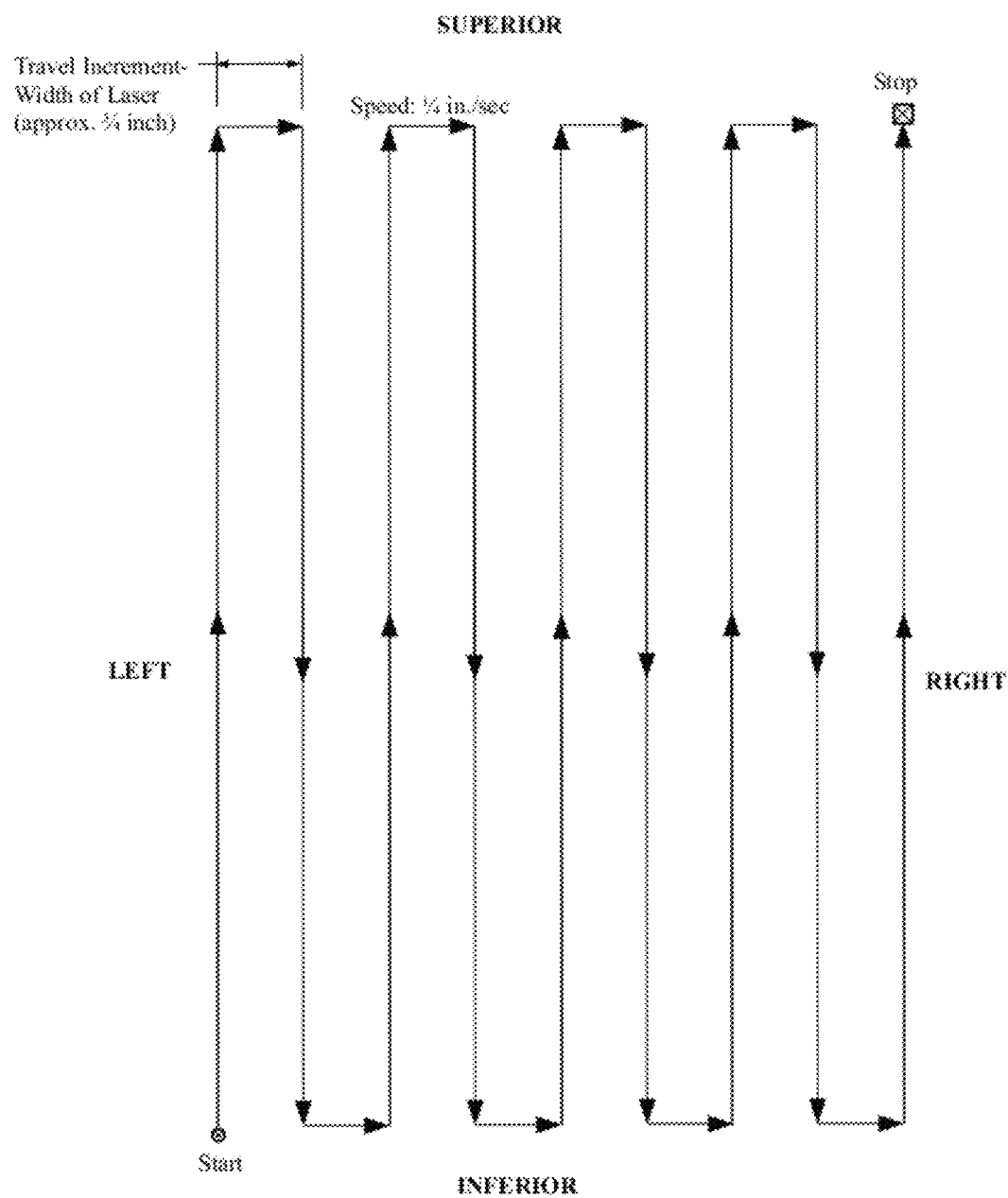
Figure 16F:
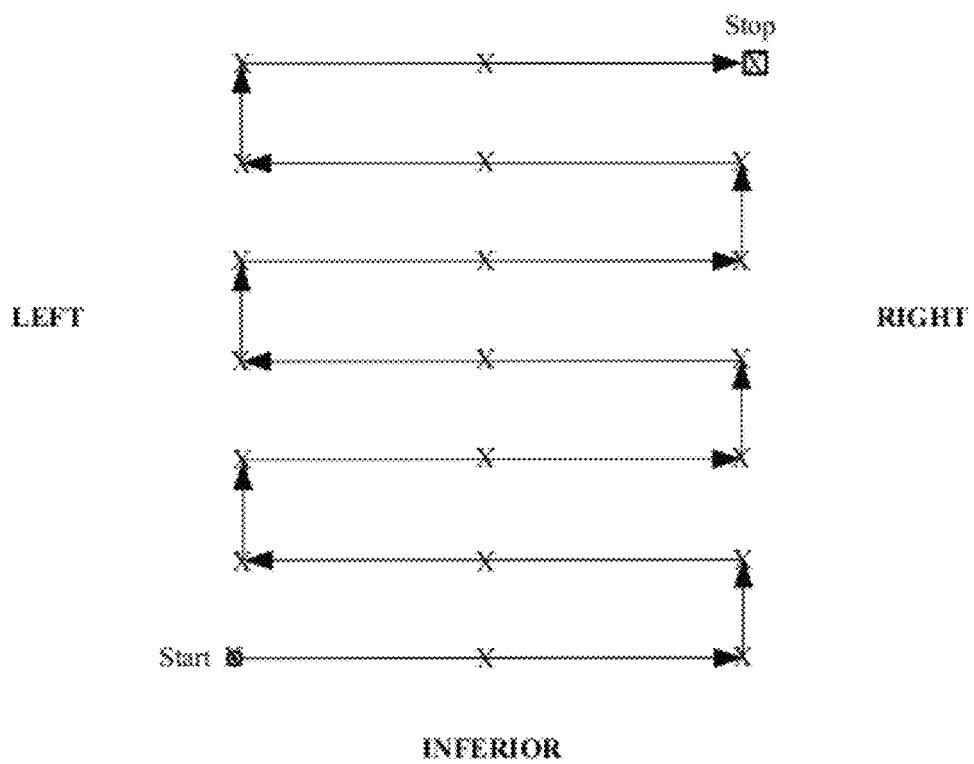
Figure 16G:
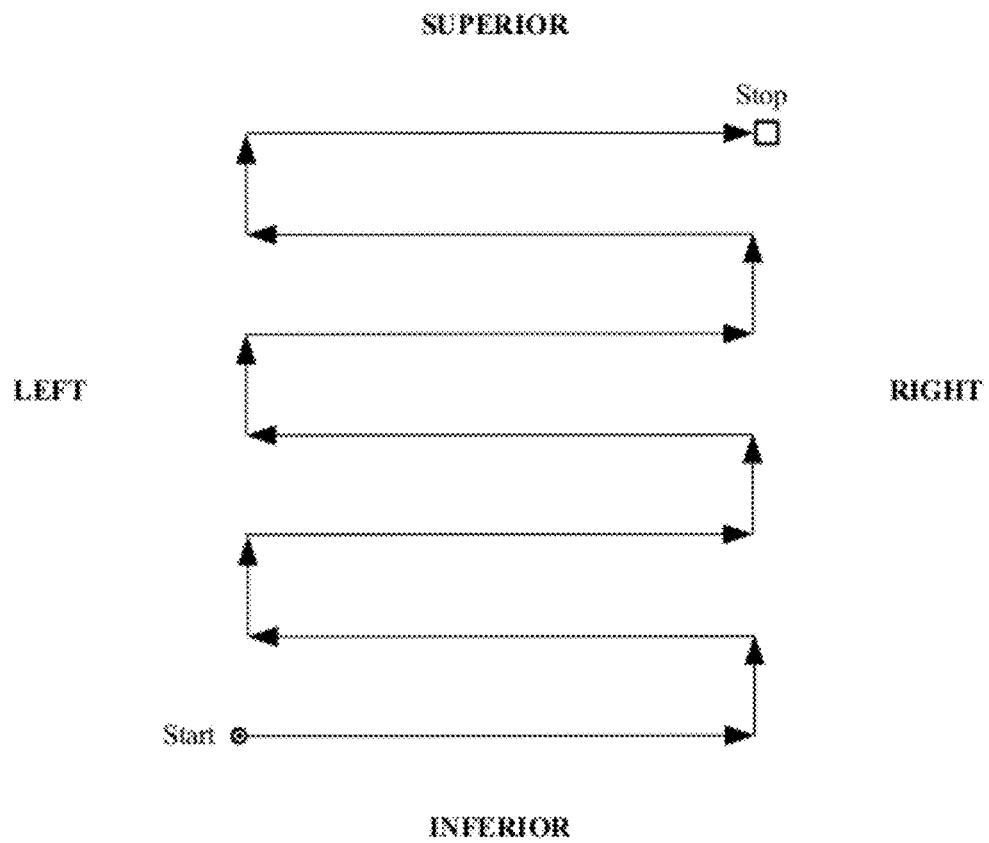
Figure 16H:
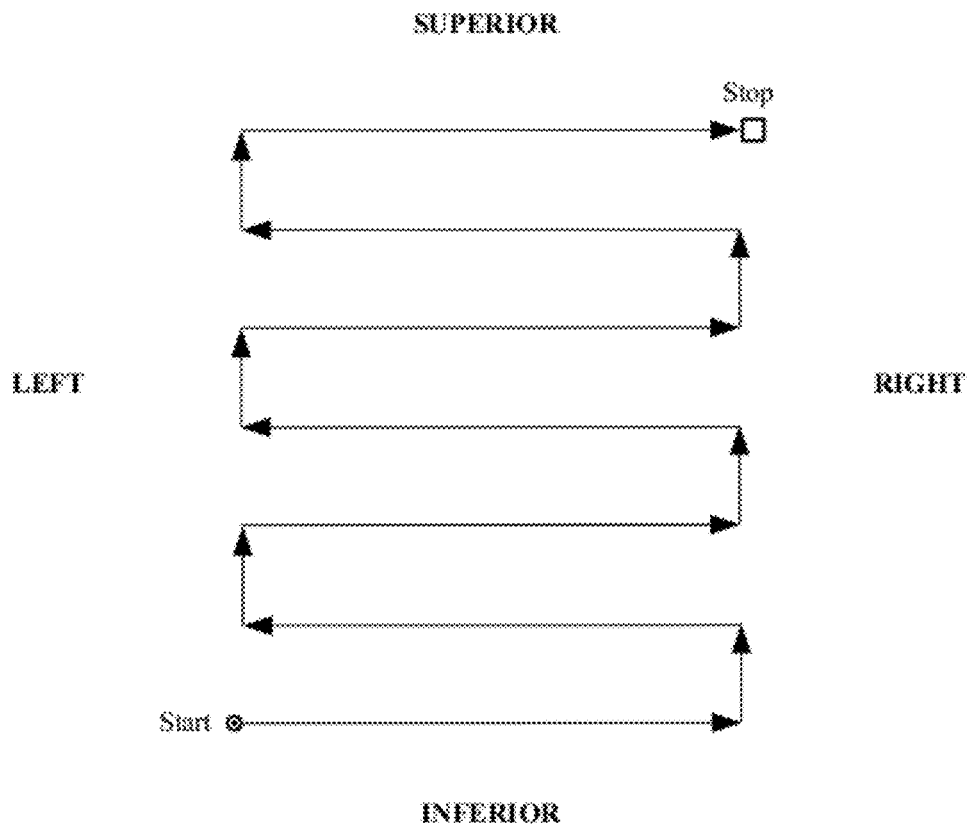
Figure 17A:
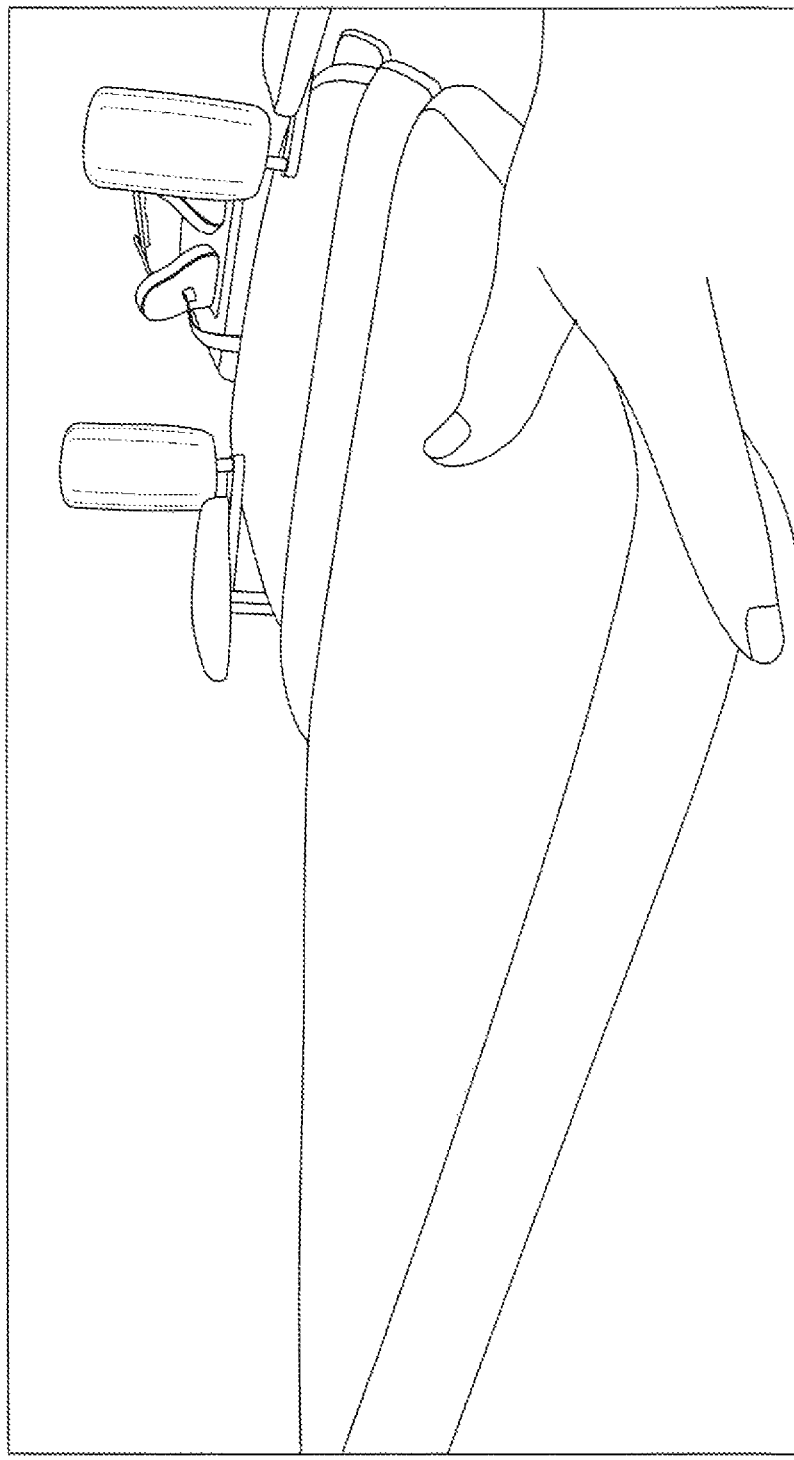
FIG. 17A shows the leg section of the treatment as it is initially being pivoted into an angled position.
Figure 17B:
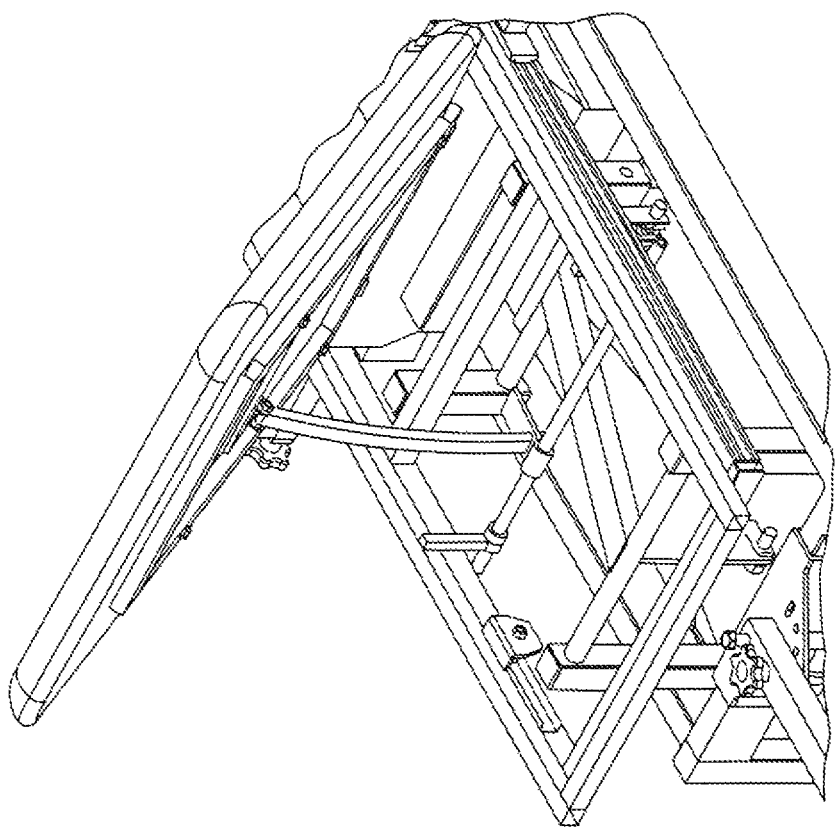
FIG. 17B shows the leg section elevated into an upward-angled position, and locked thereat using a support member.

Any of these quadrants may be selected to tailor laser application to specific region based on pain or decompression sequence In the Protocol Mode, which may be selected from an interactive screen on a computer, as seen in FIGS. 14D and 15A, there may be preprogrammed patient-specific or treatment-specific protocols—protocols usable for different regions of the body (e.g., for small joint pain in the fingers or large joint pain such as for the knee or ankle, per FIGS. 16G and 16H). With respect to spinal decompression protocols, as seen for the computer screen image of FIG. 15B, there may preferably be Five Protocols as follows:

1. Parallel Axial Laser Enhanced Spinal Decompression for Left Sided Involvement-Beginning left to right travel of the laser implement working upwards—for straight decompression protocols with left sided involvement/pain. (See e.g., FIG. 16A)
2. Parallel Axial Laser Enhanced Spinal Decompression for Right Sided Involvement-Beginning right to left travel of laser implement working upwards—for straight decompression protocols with right sided involvement/pain.
3. Lateral Axial Laser Enhanced Spinal Decompression for Right Sided Involvement-Beginning caudad to cephlad travel of laser implement moving from right to left—for right lateral flexion decompression protocols creating concentrated decompression of right spinal elements (stretching the spine into a right sided convexity). This applies laser to the right side first aiding decompression of the right sided elements. (See Motion #3A and #3B in FIGS. 16C and 16D)
4. Lateral Axial Laser Enhanced Spinal Decompression for Left Sided Involvement-Beginning caudad to cephlad travel of laser implement moving from left to right—for left lateral flexion decompression protocols creating concentrated decompression of left spinal elements (stretching the spine into a left sided convexity). This applies laser to the left side first aiding decompression of the left sided elements. (See Motion #4A and #4B in FIGS. 16E and 16D)
5. Parallel Axial Laser Enhanced Spinal Decompression with Automated Laser Acupuncture—Beginning caudad to cephlad in the centre of the laser travel moving in 1 inch increments concentrating the laser dosage at each increment for a stopping period of 15 seconds at each increment. Implement then moves to 2 inches left from centre and travels cephlad to caudad with same pattern to the bottom of the travel followed by another caudad to cephlad pattern 2 inches to right of centre. (Note an alternative "Lumbar Laser Acupuncture" protocol is illustrated in FIG. 16F).

Note, that for all protocols, the laser unit may preferably be set at 10 Watts continuous power unless a patient is sensitive to laser light or has increased melanin/darker skin tones. In these cases the laser may instead be set on the pulsed method, giving 10 Watts pulsed or a net 5 Watts.

A Central Lumbar Spinal Pain or Disc Bulge/Herniation/Stenosis Decompression Protocol may comprise: a decompression angle being arranged parallel with spine beginning at approximately 40% of a patients body weight working to approximately 70% of the patients body weight or to patient tolerance (never exceeding 85% body weight for lumbar). In some cases it will be advantageous to apply lateral decompression protocols after the 6th session to enhance paraspinal muscle flexibility. This may be applied this for a time of 8 minutes per side consecutively after an 5 minute straight decompression. This is especially advantageous for those suffering from chronic muscle hypertonicity and Osteoarthritis. Mobility is the key for these patients and this technique more effectively achieves this. The laser would be applied to the side/area being stretched. (i.e., straight decompression=central or laser across entire travel of motion device beginning from the sacrum to L1 (caudad to cephlad), decompression of right spinal elements creating right spinal convexity=laser applied to right musculature/spinal elements first working across the centre and then left lumbar spine to finish), decompression of left spinal elements creating left spinal convexity=laser applied to left musculature/spinal elements first followed by the centre and right spinal elements.)

The intent of computer controller laser therapy treatment table is to decrease treatment times and provide more effective therapy, as it allows the practitioner to apply the laser dose while the patient is under decompression, instead of prior to or following the decompression session. As the spinal segments are decompressed the laser dose can travel into the desired disc and related tissue more freely, being less inhibited by the surrounding bony structures. The laser is also intended to increase the circulation and elasticity of the involved tissues allowing the decompression treatment to be more comfortable for the patient and more thorough in its application to the desired tissues.

Optional accessories uniquely designed for mounting to the multi-functional table 10 of the current invention may comprise:

An Examination Paper Holder to provide hands-free assistance to the practitioner;

Configurations of headpiece, armrests, strapping and bolster systems that have been designed for ideal use by multiple different practitioner types (Chiropractors, Physio/Physical Therapists, Acupuncturists, Naturopathic Doctors, Massage Therapists, Athletic Therapists, Rehabilitation Specialists and Assistants, Medical Doctors and Specialists). The intent of this is to provide a system that is not only suitable for multiple practitioner use, but is ergonomically ideal for each practitioner. This creates a treatment device suitable for any practitioner in a one device one solution for multiple users using a minimal amount of valuable treatment space and time.

Leg stirrups;

Safety Side Rails—fold down or swing down;

Safety straps;

Fitted pad covers for protection;

Fitted pad covers with extra padding for treatments and other uses requiring a more comfortable patient support surface;

Treat table surfaces, components and accessories with bacteriophage for decontamination purposes; and Brand name IV-7 and the like, such as silver ion solution for decontamination purposes;

To properly enable the software that may be utilized by the present invention, which may run on a computer and/or server, or be accessed therefrom, a description of such a computer system is hereinafter disclosed. An exemplary computer system 200 is shown schematically in FIG. 5, and may comprise a computing unit 201 interacting with external devices 202, such as a separate touch screen display 245 and the laser treatment table of the current invention 241, and interacting with network resources 203, including use of the internet 262, and other computers, which may be a laptop computer 261.

The computing unit 201 may include a data bus 224 or other communication mechanism for communicating information across and among various parts of computing unit 201, and a central processing unit ("CPU" or "processor") 222 coupled with bus 224 for processing information and performing other computational and control tasks. Computing unit 201 may also include a volatile storage 225, such as a random access memory (RAM) or other dynamic storage device, coupled to bus 224 for storing various information as well as instructions to be executed by processor 222. The RAM may be Dynamic Random Access Memory (DRAM), or Static RAM (SRAM), or any other similar type of RAM known in the art. The volatile storage 225 also may be used for storing temporary variables or other intermediate information during execution of instructions by processor 222. Computing unit 201 may further include a read only memory (ROM) or an erasable programmable memory (EPROM) 227 or other static storage device coupled to bus 224 for storing static information and instructions for processor 222, such as basic input-output system (BIOS), as well as various system configuration parameters. A persistent storage device or non-volatile memory 226, such as a magnetic disk, optical disk, or solid-state flash memory device may be provided and may be coupled to bus 224 for storing information and instructions.

Computing unit 201 may be coupled via bus 224 to an integral touch screen display screen 221, such as a liquid crystal display (LCD), for displaying information to a user of the computing unit 201. If desired, the computing unit 201 may also be coupled via bus 224 to an external display screen 245. An external input device 244, including alphanumeric and other keys, may also be coupled to bus 224 for communicating information and command selections to processor 222. A cursor control device 243, such as a mouse, a trackball, or cursor direction keys for communicating direction information and command selections to processor 222 and for controlling cursor movement on display 245 or 221, may be used, if desired, as well as an external storage device 242.

According to one embodiment of the invention, the techniques described herein may be performed by computing unit 201 in response to processor 222 executing one or more sequences of one or more instructions contained in the volatile memory 225. Such instructions may be read into volatile memory 225 from another computer-readable medium, such as persistent storage device or non-volatile memory device 226. Execution of the sequences of instructions contained in the volatile memory 225 causes processor 222 to perform the process steps described herein. In alternative embodiments, hard-wired circuitry may be used in place of, or in combination with, software instructions to implement the invention.

The term "computer-readable medium" as used herein refers to any medium that participates in providing instructions to processor 222 for execution. Such a medium may take many forms, but common forms of computer-readable media include, but are not limited to: a floppy disk, a hard disk, magnetic tape, or any other magnetic medium, a CD-ROM, any other optical medium, punchcards, paper-tape, a RAM, a PROM, an EPROM, a FLASH-EPROM, a flash drive, and a memory card.

Various forms of computer readable media may be involved in carrying one or more sequences of one or more instructions to processor 222 for execution. For example, the instructions may initially be carried on a magnetic disk from a remote computer. Alternatively, a remote computer can load the instructions into its dynamic memory and send the instructions over a telephone line using a modem. A modem local to computer system 200 can receive the data on the telephone line. The bus 222 may carry the data to the volatile storage 225, from which processor 222 retrieves and executes the instructions. The instructions received by the volatile memory 225 may optionally be stored on persistent storage device 226 either before or after execution by processor 222. The instructions may also be downloaded into the computing unit 201 via the internet 261.

The computing unit 201 may also include a communication interface, such as network interface card 223 coupled to the data bus 222. Communication interface 223 may provide a two-way data communication coupling to a network link that may be connected to a local network. For example, communication interface 223 may be an integrated services digital network (ISDN) card or a modem to provide a data communication connection to a corresponding type of telephone line. As another example, communication interface 223 may be a local area network interface card (LAN NIC) to provide a data communication connection to a compatible LAN. In any such implementation, communication interface 223 sends and receives electrical, electromagnetic or optical signals that carry digital data streams representing various types of information. The network link may provide a connection over the internet 262 to the world-wide-web, to thereby access resources located anywhere. The computing unit 201 may also thereby be accessed by others with permission, such as laptop computers 261, which may be located anywhere with access to the internet 262.

Computing unit 201 may be able to send messages and receive data, including program code, through the variety of network(s) including the Internet 262, network link and communication interface 223. Similarly, it may receive code from other network resources. The received code may be executed by processor 222 as it is received, and/or stored in persistent or volatile storage devices 226 and 225, respectively, or other non-volatile storage for later execution. In this manner, computer system 200 may obtain application code fro remote sources.

The examples and descriptions provided merely illustrate a preferred embodiment of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

I claim:

1. A computer-controllable laser therapy treatment table, for use in providing non-surgical spinal decompression laser treatment protocols to treat soft tissue damage and herniated disks, said computer-controllable laser therapy treatment table comprising:
   a frame having a first end, a second end, a top and a bottom;
   a body support table, said body support table being secured to said frame, said body support table having an opening in said table being at a distance from a periphery of said body support table;
   an enclosure with an opening into a cavity therein, a portion of said enclosure being fixedly secured to an underside of said body support table, with at least a portion of said opening in said enclosure configured to interconnect with said opening in said body support table;
   a first linear actuator secured within said cavity of said enclosure and being adapted to drive a carriage on said first linear actuator in a positive and/or negative X-direction;
   a second linear actuator having a portion being secured to said carriage of said first linear actuator to thereby be movable in the X-direction, and with said second linear actuator being adapted to drive a carriage on said second actuator in a positive or negative Y-direction, said carriage of said second actuator thereby being capable of simultaneous motion in both the X and Y directions;
   a laser hand-piece comprising a class 4 medical laser, said class 4 medical laser comprising a lens configured to diverge a beam of laser light from said laser to be at an optimal angle, and to maintain a uniform dosage intensity across a width of said beam;
   an attachment means being secured to said carriage of said second linear actuator and configured for thereon providing releasable support for said laser hand-piece;
   a cushioned gland with a portion being fixedly secured to a top of said body support table, over an entire perimeter of said opening in said body support table, said cushioned gland comprising an opening, at least a portion of said opening in said cushioned gland configured to interconnect with said opening in said body support table; said cushioned gland configured to seal said enclosure and said body support table against a patient's spinal region to prevent laser light from escaping therefrom;
   a motion controller configured to control said first and second linear actuators, and being usable to position said laser hand-piece along an X direction and along a Y direction and to selectively engage said laser hand-piece to emit laser light through said opening in said enclosure, and to track according to a specific pattern of motion according to one or more pre-programmed treatment protocols to thereby treat spinal soft tissue damage and herniated disks;
   a spinal traction system configured to concurrently provide traction to a region of a patient's spine; and
   an adjustable cervical support section comprising:
      a plate mounted to said frame to pivot about a first axis, to permit upward angular adjustment of said plate with respect to said frame;
      means for releasably locking said pivotal plate at a desired said upward angular adjustment about said first axis;
      a tray mounted to said plate to pivot about a second axis, to permit lateral angular adjustment of said tray with respect to said plate, to facilitate lateral cervical spinal decompression; said tray comprising one or more tracks;
      means for releasably locking said pivotal tray at a desired said lateral angular adjustment about said second axis;
      one or more rollers rotatably mounted to said plate to rotatably support said pivotal tray;

a padded head support mounted to said tray to be slidable in said one or more tracks with respect to said frame;

a first neck bolster and a second neck bolster, each mounted to said padded head support to slide laterally, to respectively support a first side and a second side of the patients' neck;

a scissors mechanism configured to simultaneously adjust said first and second neck bolsters to respectively slide to a desired neck support position;

a three-point cervical strap system comprising:
- a forehead strap secured to said padded head support, and configured to be secured over the forehead of the patient; and
- a first bolster strap and a second bolster strap, each said first and second bolster straps having a first end respectively secured to said first and second bolsters, and with each having a second end comprising means for releasably securing said second end to said over-forehead strap;

and means for incrementally sliding said padded head support away from said frame, to facilitate axial cervical traction.

2. The computer-controllable laser therapy treatment table according to claim 1 further comprising one or more temperature sensors configured for thermographic imaging to monitor tissue temperatures to achieve an optimal laser light dosage for said pre-programmed treatment protocol.

3. The computer-controllable laser therapy treatment table according to claim 1 further comprising one or more proximity sensors positioned near said opening in said enclosure and configured to detect a patient thereon, said one or more proximity sensors coupled to a relay or a switch configured to shut down said emitted laser light when said one or more proximity switches fail to detect the patient upon said opening.

4. The computer-controllable laser therapy treatment table according to claim 1 wherein said laser is configured to emit light at one or more wavelengths to provide a depth of penetration of approximately 10 cm on a full power setting for treatment of spinal and joint conditions.

5. The computer-controllable laser therapy treatment table according to claim 4 wherein said laser is configured to deliver 620 joules per minute of energy, and is configured to emit light at a wavelength of 940 nm +/− 15 nm.

6. The computer-controllable laser therapy treatment table according to claim 1 further comprising a pair of cylindrical arm support bolsters configured to protrude above said top of said body support table, and means for adjustably securing said pair of arm bolsters to said frame to permit incremental adjustments both cephalically and caudally, and incremental adjustments both medially and laterally.

7. The computer-controllable laser therapy treatment table according to claim 1 wherein said treatment protocol comprises a lumbar protocol, said lumbar protocol comprising:

said motion controller configured to control said first and second linear actuators for said pattern of motion of said laser to comprise incremental movement between a plurality of positions to form a ladder pattern, with said laser to alternate movement for each of 7 steps of said ladder pattern between lateral movement left-to-right and lateral movement right-to-left, for said laser to progressively travel between each said step from an inferior lumbar position towards a superior lumbar position; and with said laser to begin 2 inches left of center at a start position on a first said step, and to move 2 inches to the right to a central position, and to subsequently move 2 inches right of center, for said first said step of said ladder pattern; with each subsequent said lateral movement for each step in the right-to-left direction and in the left-to-right direction each similarly comprising 3 positions and 2 increments therebetween, with each increment comprising 2 inches of movement, for a total lateral movement of 4 inches for each said step; and with a distance of incremental travel between each said step to equal a width of said laser beam;

said motion controller configured to control said first and second linear actuators for said pattern of motion of said laser to comprise a dwell time of 10 seconds for said laser at each of said plurality of positions; and said motion controller configured to control said first and second linear actuators for said pattern of motion of said laser to comprise said laser to move at one-quarter of an inch per second between each of said plurality of positions.

8. The computer-controllable laser therapy treatment table according to claim 7 wherein said width of said laser beam is 1 inch, and said 7 steps of said progressive inferior-to-superior travel comprises a total of 6 inches of travel.

9. The computer-controllable laser therapy treatment table according to claim 7 wherein said traction for said lumbar protocol comprises a traction amount being between 40% of the patient's body weight and 70% of the patient's body weight.

10. The computer-controllable laser therapy treatment table according to claim 7 wherein said class IV laser is configured to emit 10 Watts continuous power for said lumbar protocol.

11. The computer-controllable laser therapy treatment table according to claim 7 wherein said class IV laser is configured to emit 10 Watts of pulsed power for said lumbar protocol.

12. A computer-controlled treatment table, for simultaneous application of traction and laser light treatment to a patient's spine, said treatment table comprising:

a table having an opening therein;

means for providing traction to a portion of the patient's spine positioned across said opening of said table;

a class 4 medical laser, said class 4 medical laser comprising a lens configured to diverge a beam of light from said laser to be at an optimal angle, and to maintain a uniform dosage intensity across a width of said beam;

means for translating said laser for selectively directing a beam of light emitted therefrom through said opening in said table and onto the patient; and a motion controller configured to control said means for translating said laser, for said selective directing of said beam of laser light to thereby track in a pattern of motion across the skin proximate to the spinal portion of the patient to be treated, according to a pre-programmed laser therapy treatment protocol, in combination with said spinal traction;

a cushioned gland with an opening therein, said cushioned gland fixedly secured on a top of said table, over an entire perimeter of said opening in said table, for said opening in said gland to interconnect with said opening in said table;

an enclosure with an opening into a cavity, said enclosure fixedly secured to, and sealed against, an underside of said table, for said opening in said enclosure to interconnect with said interconnected openings of said table and cushioned gland;

wherein said means for translating said laser is configured to translate said laser within said enclosure, for said beam of light from said laser to be selectively directed out through said interconnected openings; said cushioned gland configured to seal against the patient's back to seal said enclosure to prevent laser light from escaping therefrom; and wherein said treatment protocol comprises a lumbar protocol, said lumbar protocol comprising:

said motion controller configured to control said first and second linear actuators for said pattern of motion of said laser to comprise incremental movement between a plurality of positions to form a ladder pattern, with said laser to alternate movement for each of 7steps of said ladder pattern between lateral movement left-to-right and lateral movement right-to-left, for said laser to progressively travel between each said step from an inferior lumbar position towards a superior lumbar position; and with said laser to begin 2 inches left of center at a start position on a first said step, and to move 2inches to the right to a central position, and to subsequently move 2 inches right of center, for said first said step of said ladder pattern, with each subsequent said lateral movement for each step in the right-to-left direction and in the left-to-right direction each similarly comprising 3 positions and 2 increments therebetween, with each increment comprising 2 inches of movement, for a total lateral movement of 4 inches for each said step; and with a distance of incremental travel between each said step to equal a width of said laser beam;

said motion controller configured to control said first and second linear actuators for said pattern of motion of said laser to comprise a dwell time of 10 seconds for said laser at each of said plurality of positions; and said motion controller configured to control said first and second linear actuators for said pattern of motion of said laser to comprise said laser to move at one-quarter of an inch per second between each of said plurality of positions.

13. The computer-controlled treatment table according to claim 12 further comprising one or more proximity sensors positioned near said opening in said table, and configured to detect the patient, said one or more proximity sensors coupled to a switch configured to shut down said laser when said one or more proximity switches fail to detect the patient upon said opening.

14. The computer-controlled treatment table according to claim 12 further comprising one or more temperature sensors configured for thermographic imaging, to monitor tissue temperatures to achieve an optimal dosage for said pre-programmed laser light treatment protocol.

15. The computer-controlled treatment table according to claim 12, wherein said width of said laser beam is 1 inch, and said 7 steps of said progressive inferior-to-superior travel comprises a total of 6 inches of travel; and wherein said traction for said lumbar protocol comprises a traction amount being between 40% of the patient's body weight and 70% of the patient's body weight.

16. The computer-controlled treatment table according to claim 12 wherein said class IV laser is configured to emit 10 Watts continuous power for said lumbar protocol.

17. The computer-controlled treatment table according to claim 12 wherein said class IV laser is configured to emit 10 Watts of pulsed power for said lumbar protocol.

18. The computer-controlled treatment table according to claim 12 further comprising an adjustable cervical support section, said adjustable cervical support section comprising:

a plate mounted to said table to pivot about a first axis, to permit upward angular adjustment of said plate with respect to said table;

means for releasably locking said pivotal plate at a desired said upward angular adjustment about said first axis;

a tray mounted to said plate to pivot about a second axis, to permit lateral angular adjustment of said tray with respect to said plate, to facilitate lateral cervical spinal decompression; said tray comprising one or more tracks;

means for releasably locking said pivotal tray at a desired said lateral angular adjustment about said second axis;

one or more rollers rotatably mounted to said plate to rotatably support said pivotal tray;

a padded head support mounted to said tray to be slidable in said one or more tracks with respect to said frame;

a first neck bolster and a second neck bolster, each mounted to said padded head support to slide laterally, to support a first side and a second side of the patients' neck;

a scissors mechanism configured to simultaneously adjust said first and second neck bolsters to respectively slide to a desired neck support position;

a three-point cervical strap system comprising:

a forehead strap secured to said padded head support, and configured to be secured over the forehead of the patient; and a first bolster strap and a second bolster strap, each said first and second bolster straps having a first end respectively secured to said first and second bolsters, and with each having a second end comprising means for releasably securing said second end to said over-forehead strap;

and means for incrementally sliding said padded head support relative to said tray, to facilitate axial cervical traction.

* * * * *